United States Patent
Yoakim et al.

(10) Patent No.: US 6,242,439 B1
(45) Date of Patent: Jun. 5, 2001

(54) AZETIDINONE DERIVATIVES FOR THE TREATMENT OF HCMV INFECTIONS

(75) Inventors: Christiane Yoakim, Laval; Robert Déziel, Mont-Royal; Jeffrey O'Meara, Laval; William W. Ogilvie, Rosemére, all of (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 0 days.

(21) Appl. No.: 09/167,143

(22) Filed: Oct. 6, 1998

Related U.S. Application Data

(60) Provisional application No. 60/061,544, filed on Oct. 7, 1997.

(51) Int. Cl.$^7$ ............... A61K 31/397; A61P 31/22; C07D 407/06; C07D 403/06; C07D 205/00
(52) U.S. Cl. ....................... 514/210.02; 540/200
(58) Field of Search ............... 540/200; 514/210, 514/210.02

(56) References Cited

U.S. PATENT DOCUMENTS

| 5,100,880 | 3/1992 | Durette et al. ............ 540/360 |
| 5,104,862 | 4/1992 | Durette et al. ............ 540/360 |
| 5,229,831 | 7/1993 | Doherty et al. ............ 540/300 |

FOREIGN PATENT DOCUMENTS

| 0199630 | 10/1986 | (EP) . |
| 0377549 | 10/1989 | (EP) . |
| 2266527 | 11/1993 | (GB) . |
| WO 95/02579 | 1/1995 | (WO) . |

OTHER PUBLICATIONS

Hagmann et al., Bioog. Med Chem. Lett, 1992, vol. 2, p. 681.
Hagmann et al., J. Med. Chem. 1993, vol. 36, p. 771.
Shah et al., Bioorg. Med. Chem. Lett. 1993, vol. 3, p. 2295.
Finke et al., J. Med. Chem. 1995, vol. 38, p. 2449.
Kobayashi et al., Chemical Abstracts, vol. 124, Abs. 29520, 1996 for Japanese Patent Application 07242624 published Sep. 19, 1995 (Nippon Tabacco).
Boeheme et al., Annual Reports in Medicinal Chemistry, 1995, vol. 30, p. 139.

Primary Examiner—Mark Berch
(74) Attorney, Agent, or Firm—Robert P. Raymond; Alan R. Stempel; Mary-Ellen M. Devlin

(57) ABSTRACT

A compound of formula I

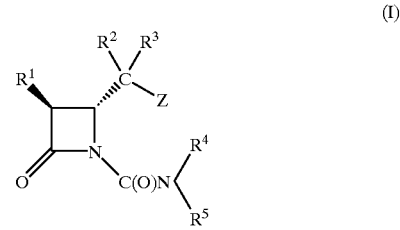

wherein $R^1$ is hydrogen, methyl, ethyl, methoxy or methylthio; $R^2$ and $R^3$ each independently is hydrogen or lower alkyl; $R^4$ is hydrogen, lower alkyl, methoxy, ethoxy or benzyloxy; $R^5$ is lower alkyl, lower cycloalkyl, $(CH_2)_mC(O)OR^6$ wherein m is the integer 1 or 2 and $R^6$ is lower alkyl, phenyl optionally substituted; optionally Het or Het(lower alkyl); or $R^4$ and $R^5$ together with the nitrogen atom to which they are attached form a nitrogen containing ring optionally substituted with C(O)O-benzyl or with phenyl optionally substituted with $C(O)OR_7$ wherein $R_7$ is lower alkyl or (lower alkyl)phenyl; and Z is lower alkyl or optionally substituted phenyl or Het; with the proviso that when Z is $(CH_2)_p$-(Het), then $R^2$ and $R^3$ each is hydrogen; or a therapeutically acceptable acid addition salt thereof which compound is useful in the treatment of HCMV infections.

11 Claims, No Drawings

AZETIDINONE DERIVATIVES FOR THE TREATMENT OF HCMV INFECTIONS

This application claims the benefit under 35 U.S.C. §119 (e) of prior U.S. Provisional Application No. 60/061,544 filed Oct. 7, 1997.

FIELD OF THE INVENTION

This invention relates to azetidinone derivatives having activity against herpes infections. More specifically, the invention relates to azetidin-2-one derivatives exhibiting antiherpes activity, to pharmaceutical compositions comprising the derivatives, and methods of using the derivatives to inhibit the replication of herpes virus and to treat herpes infections.

BACKGROUND OF THE INVENTION

Herpes viruses inflict a wide range of diseases against humans and animals. For instance, herpes simplex viruses, types 1 and 2 (HSV-1 and HSV-2), are responsible for cold sores and genital lesions, respectively; varicella zoster virus (VZV) causes chicken pox and shingles; and the human cytomegalovirus (HCMV) is a leading cause of opportunistic infections in immunosuppressed individuals.

Over the past two decades, a class of compounds known as the purine and pyrimidine nucleoside analogs has received the most attention by investigators in the search for new therapeutic agents for treatment of herpes virus infections. As a result, several nucleoside analogs have been developed as antiviral agents. The most successful to date is acyclovir which is the agent of choice for treating genital HSV infections. Another nucleoside analog, ganciclovir, has been used with some success in treating HCMV infections.

Nevertheless, in spite of some significant advances, the need for effective, safe therapeutic agents for treating herpes viral infections continues to exist. For a review of current therapeutic agents in this area, see R. E. Boeheme et al., Annual Reports in Medicinal Chemistry, 1995, 30, 139.

Azetidin-2-one derivatives have been reported in the literature as having a variety of biological activities; mainly antibacterial, antiinflammatory, antidegenerative, etc. However, azetidin-2-one derivatives have not been reported to be antiviral agents against herpes viruses.

The following references disclose azetidin-2-ones having biological activity:

S. K. Shah et al., European patent application 0,199,630, Oct. 29, 1986,
S. K. Shah et al., European patent application 0,377,549, Oct. 18, 1989,
P. L. Durette and M. Maccoss, U.S. Pat. No. 5,100,880, Mar. 31, 1992,
P. L. Durette and M. Maccoss, U.S. Pat. No. 5,104,862, Apr. 14, 1992,
W. K. Hagmann et al., Bioorg. Med. Chem. Lett. 1992, 2, 681,
W. K. Hagmann et al., J. Med. Chem. 1993, 36, 771, J. B. Doherty et al., U.S. Pat. No. 5,229,381, issued Jul. 20, 1993,
S. K. Shah et al., Bioorg. Med. Chem. Lett. 1993, 3, 2295,
G. Crawley, PCT patent WO 95/02579, published Jan. 26, 1995,
P. E. Finke et al., J. Med. Chem. 1995, 38, 2449, and K. Kobayashi et al., Japanese patent application 07242624, published Sep. 19, 1995; Chem. Abstr. 1996, 124, 29520.

SUMMARY OF THE INVENTION

The present application discloses a group of azetidin-2-one derivatives particularly active against cytomegalovirus. This activity coupled with a wide margin of safety, renders these derivatives desirable agents for combating herpes infections.

The present azetidin-2-one derivatives are distinguished from the prior art compounds in that they possess different chemical structures and biological activities.

The azetidin-2-one derivatives are represented by formula 1:

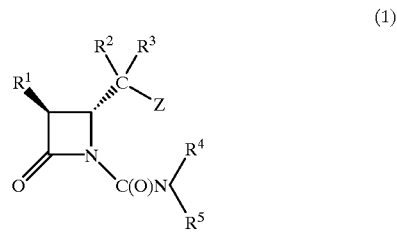

wherein $R^1$ is hydrogen, methyl, ethyl, methoxy or methylthio;

$R^2$ and $R^3$ each independently is hydrogen or lower alkyl;

$R^4$ is hydrogen, lower alkyl, methoxy, ethoxy or benzyloxy;

$R^5$ is lower alkyl, lower cycloalkyl, $(CH_2)_mC(O)OR^6$ wherein m is the integer 1 or 2 and $R^6$ is lower alkyl or phenyl(lower alkyl);

phenyl, phenyl monosubstituted, disubstituted or trisubstituted with a substituent selected independently from the group consisting of lower alkyl, lower alkoxy, lower alkylthio, halo, hydroxy and amino; phenyl(lower alkyl), phenyl(lower alkyl) monosubstituted or disubstituted on the phenyl portion thereof with a substituent selected independently from the group consisting of lower alkyl, lower alkoxy, lower alkylthio, halo, hydroxy, nitro, amino, lower alkylamino, di(lower alkyl)amino, lower alkyl-C(O)NH, di(lower alkyl)aminocarbonyl, cyano, trifluoromethyl, (trifluoromethyl)thio, (trifluoromethyl)sulfinyl, (trifluoromethyl)sulfonyl and $C(O)OR^7$ wherein $R^7$ is lower alkyl or phenyl (lower alkyl);

Het or Het(lower alkyl) wherein Het represents an unsubstituted, monosubstituted or disubstituted five or six membered, monovalent heterocyclic ring containing one or two heteroatoms selected from the group consisting of N, O or S, wherein each substituent is selected independently from the group consisting of lower alkyl, lower alkoxy, halo and hydroxy;

5-(benzo[1,3]dioxolyl)methyl, (1(R)-1-naphthalenyl) ethyl, 2-benzothiazolyl or 2-thiazolo[4,5-b] pyridinyl; or $R^4$ and $R^5$ together with the nitrogen atom to which they are attached form a piperidino, morpholino, thiomorpholino, piperazino, N-methylpiperazino, 1-(3, 4-dihydro-1H-isoquinolinyl) or 2-(3,4-dihydro-1H-isoquinolinyl) or a pyrrolidino ring optionally substituted with benzyloxycarbonyl or with phenyl said phenyl ring optionally mono- or di-substituted with a substituent selected independently from the group consisting of lower alkyl, lower alkoxy, lower alkylthio, halo, hydroxy, nitro, amino, lower alkylamino, di(lower alkyl)amino, lower alkyl-C(O)NH, di(lower alkyl) aminocarbonyl, cyano, trifluoromethyl, (trifluoromethyl)thio, (trifluoromethyl)sulfinyl, (trifluoromethyl)sulfonyl and C(O)OR$_7$ wherein R$_7$ is lower alkyl or (lower alkyl)phenyl; and Z is lower alkyl, phenyl, phenyl monosubstituted or disubstituted with a substituent selected independently from lower alkyl, lower alkoxy, halo, hydroxy and amino; phenylmethyl, phenylmethyl mono-substituted or disubstituted on the phenyl portion thereof with a substituent selected from the group consisting of lower alkyl, lower alkoxy, halo, hydroxy and amino; or (CH$_2$)$_p$-(Het) wherein p is the integer 0 or 1 and Het is as defined herein; with the proviso that when Z is (CH$_2$)$_p$-(Het) as defined herein then R$^2$ and R$^3$ each is hydrogen;

or a therapeutically acceptable acid addition salt thereof.

A preferred group of compounds is represented by formula 1 wherein R$^1$, R$^2$ and R$^3$ are as defined hereinabove;

R$^4$ is hydrogen or lower alkyl;

R$^5$ is lower alkyl, lower cycloalkyl, CH$_2$C(O)OR$^6$ wherein R$^6$ is methyl, ethyl or phenylmethyl; phenyl, phenyl monosubstituted, disubstituted or trisubstituted with a substituent selected independently from the group consisting of lower alkyl, lower alkoxy, lower alkylthio, halo, hydroxy and amino; phenyl(lower alkyl), phenyl(lower alkyl) monosubstituted or disubstituted on the phenyl portion thereof with a substituent selected independently from the group consisting of lower alkyl, lower alkoxy, lower alkylthio, halo, hydroxy, nitro, amino, lower alkylamino, di(lower alkyl)amino, lower alkyl-C(O)NH, di(lower alkyl) aminocarbonyl, cyano, trifluoromethyl, (trifluoromethyl)thio, (trifluoromethyl)sulfinyl, (trifluoromethyl)sulfonyl and C(O)OR$^7$ wherein R$^7$ is methyl, ethyl or phenylmethyl; Het or Het(lower alkyl) wherein Het is 2-furyl, 2-methyl-3-furyl, 2-thienyl, 2-pyridinyl, 3-pyridinyl, 4-pyridinyl, 3-methyl-2-pyrrolyl, 2-thiazolyl, 4-thiazolyl, 2-isoxazolyl, 2-pyrimidinyl, 4-methyl-2-pyrimidinyl, 4,6-dimethyl-2-pyrimidinyl, 4-pyrimidinyl, 2,6-dimethyl-2-pyrimidinyl, 4-methyltetrazolyl, 2-benzothiazolyl or 2-thiazolo[4,5-b]pyridinyl; (5-benzo[1,3]dioxolyl) methyl, 1(R)-(1-naphthalenyl)ethyl; or R$^4$ and R$^5$ together with the nitrogen atom to which they are attached form a pyrrolidino, piperidino, morpholino, N-methylpiperazino, 1-(3,4-dihydro-1H-isoquinolinyl) or 2-(3,4-dihydro-1H-isoquinolinyl);

and Z is as defined hereinabove.

A more preferred group of compounds is represented by formula 1 wherein R$^1$ is hydrogen, methyl, ethyl, methoxy or methylthio;

R$^2$ and R$^3$ each independently is hydrogen, or methyl;

R$^4$ is hydrogen, methyl, or ethyl;

R$^5$ is methyl, ethyl, 1-methylethyl, cyclobutyl, cyclopentyl, cyclohexyl, CH$_2$C(O)OR$^6$ wherein R$^6$ is methyl or phenylmethyl; phenyl, 4-fluorophenyl, 4-methoxyphenyl, 3,5-dimethyl-4-methoxyphenyl, 4-methylphenyl, 4-(methylthio)phenyl, phenylmethyl, phenylethyl, 1-phenylpropyl, 1-phenylbutyl, phenylmethyl monosubstituted at position 3 or 4 of the phenyl portion thereof with a substituent selected from the group consisting of methyl, ethyl, 1-methylethyl, 1,1-dimethylethyl, propyl, methoxy, ethoxy, methylthio, bromo, chloro, fluoro, nitro, acetamido, C(O)NMe$_2$, C(O)NEt$_2$, cyano, trifluoromethyl, (trifluoromethyl) thio, (trifluoromethyl)sulfinyl, (trifluoromethyl) sulfonyl and C(O)OR$^7$ wherein R$^7$ is methyl, ethyl or benzyl;

(5-benzo[1,3]dioxolyl)methyl, 1(R)-(1-naphthylenyl) ethyl, 2-pyridinyl, 4-pyridinyl, 2-pyridinylmethyl, 4-pyridinylmethyl, 1-(4-pyridinyl)ethyl or 1-(4-pyridinyl)propyl; or R$^4$ and R$^5$ together with the nitrogen to which they are attached form a pyrrolidino, piperidino, morpholino, 1-(3,4-dihydro-1H-isoquinolinyl) or 2-(3,4-dihydro-1H-isoquinolinyl); and Z is phenyl or phenylmethyl.

Another more preferred group of compounds is represented by formula 1 wherein R$^1$ is hydrogen, methyl or methylthio;

R$^2$ and R$^3$ each independently is hydrogen or methyl;

R$^4$ is hydrogen, methyl or ethyl;

R$^5$ is methyl, ethyl, 1-methylethyl, cyclobutyl, cyclopentyl, cyclohexyl, CH$_2$C(O)OR$^6$ wherein R$^6$is methyl or phenylmethyl; phenyl, 4-fluorophenyl, 4-methoxyphenyl, 3,5-dimethyl-4-methoxyphenyl, 4-methylphenyl, 4-(methylthio)phenyl, phenylmethyl, 1-phenylpropyl, 1-phenylbutyl, phenylmethyl monosubstituted at position 3 or 4 of the phenyl portion thereof with a substituent selected from the group consisting of methyl, ethyl, 1-methylethyl, 1,1-dimethylethyl, propyl, methoxy, ethoxy, methylthio, bromo, chloro, fluoro, nitro, acetamido, C(O)NMe$_2$, C(O)NEt$_2$, cyano, trifluoromethyl, (trifluoromethyl) thio, (trifluoromethyl)sulfinyl, (trifluoromethyl) sulfonyl and C(O)OR$^7$ wherein R$^7$ is methyl, ethyl or benzyl; (5-benzo[1,3]dioxolyl)methyl, 1(R)-(1-naphthalenyl)ethyl, 2-pyridinyl, 4-pyridinyl, 2-pyridinylmethyl, 4-pyridinylmethyl, 1-(4-pyridinyl) ethyl or 1-(4-pyridinyl)propyl; and Z is lower alkyl.

Still another more preferred group of compounds is represented by formula 1 wherein R$^1$ is hydrogen, methyl, methylthio or methoxy;

R$^2$ and R$^3$ each independently is hydrogen or methyl;

R$^4$ is hydrogen, methyl or ethyl;

R$^5$ is methyl, ethyl, 1-methylethyl, cyclobutyl, cyclopentyl, cyclohexyl, CH$_2$C(O)OR$^6$ wherein R$^6$ is methyl or phenylmethyl; phenyl, 4-fluorophenyl, 4-methoxyphenyl, 3,5-dimethyl-4-methoxyphenyl, 4-methylphenyl, 4-(methylthio)phenyl, phenylmethyl, 1-phenylpropyl, 1-phenylbutyl, phenylmethyl monosubstituted at position 3 or 4 of the phenyl portion thereof with a substituent selected from the group consisting of methyl, ethyl, 1-methylethyl, 1,1-dimethylethyl, propyl, methoxy, ethoxy, methylthio, bromo, chloro, fluoro, nitro, acetamido, C(O)NMe$_2$, C(O)NEt$_2$, cyano, trifluoromethyl, (trifluoromethyl) thio, (trifluoromethyl)sulfinyl, (trifluoromethyl) sulfonyl and C(O)OR$^7$ wherein R$^7$ is methyl, ethyl or benzyl; (5-benzo[1,3]dioxolyl)methyl, 1(R)-(1-naphthalenyl)ethyl, 2-pyridinyl, 4-pyridinyl, 2-pyridinylmethyl, 4-pyridinylmethyl, 1-(4-pyridinyl) ethyl or 1-(4-pyridinyl)propyl; and Z is 2-furyl, 2-thienyl, 2-pyridinyl, 3-pyridinyl, 4-pyridinyl, 3-methyl-2-pyrrolyl, 2-thiazolyl, 2-isoxazolyl, 2-pyrimidinyl, 4,6-dimethyl-2-pyrimidinyl, 5-(1-methyl-1H-tetrazolyl), 5-(2-methyl-2H-tetrazolyl), 2-benzothiazolyl or 2-thiazolo[4,5-b] pyridinyl.

A most preferred group of compounds is represented by formula 1 wherein R$^1$ is hydrogen, methyl, methoxy or methylthio;

$R^2$ and $R^3$ each is hydrogen;

$R^4$ is hydrogen or methyl;

$R^5$ is $CH_2C(O)OR^6$ wherein $R^6$ is phenylmethyl; or $R^5$ is 4-fluorophenyl, 4-methoxyphenyl, 3,5-dimethyl-4-methoxyphenyl, (4-methylthio)phenyl, phenylmethyl, 1(R)-phenylethyl, 1(S)-phenylethyl, 1(R)-phenylpropyl, 1(R)-phenylbutyl, (4-methylphenyl)methyl, {4-(1-methylethyl)phenyl}methyl, (4-methoxyphenyl)methyl, (4-chlorophenyl)methyl, (2-nitrophenyl)methyl, (3-nitrophenyl)methyl, {4-(acetylamino)phenyl}methyl, {4-(trifluoromethyl)phenyl}methyl, {4-{(trifluoromethyl)thio}phenyl}methyl, {4-{(trifluoromethyl)sulfinyl}phenyl}methyl, {4-{(trifluoromethyl)sulfonyl}phenyl}methyl, {4-(methoxycarbonyl)phenyl}methyl, (5-benzo[1,3]dioxolyl)methyl, 1(R)-(1-naphthalenyl)ethyl, 4-pyridinyl, 4-pyridinylmethyl or 1-(4-pyridinyl)propyl; or $R^4$ and $R^5$ together with the nitrogen to which they are attached form a pyrrolidino, morpholino, 1-(3,4-dihydro-1H-isoquinolinyl) or 2-(3,4-dihydro-1H-isoquinolinyl); and Z is phenyl or phenylmethyl.

Included within the scope of this invention is a pharmaceutical composition for treating cytomegalovirus infections in a human comprising a compound of formula 1, or a therapeutically acceptable salt thereof, and a pharmaceutically acceptable carrier.

The scope of the invention also includes a method for treating cytomegalovirus infections in a human comprising administering thereto an effective amount of the compound of formula 1, or a therapeutically acceptable salt thereof.

Also included within the scope is a method for protecting human cells against cytomegalovirus pathogenesis comprising treating said cells with an anti-cytomegalovirus effective amount of a compound of formula 1, or a therapeutically acceptable salt thereof.

Compounds of formula I according to the present invention may also be used in co-therapies with other conventional anti-herpes compounds, such as but not limited to ganciclovir, foscarnet, acyclovir, valacyclovir, famciclovir, cidofovir, penciclovir, and lobucavir.

Compounds of formula I according to the present invention may also be used in co-therapies with anti-retroviral compounds such as reverse transcriptase inhibitors (i.e. AZT, 3TC) or protease inhibitors.

Process for preparing the compounds of formula 1 are described hereinafter.

DETAILED DESCRIPTION OF THE INVENTION

General

As used herein, the following definitions apply unless otherwise noted:

With reference to the instances where (R) or (S) is used to designate the configuration of a radical, e.g. $R^5$ of the compound of formula 1, the designation is done in the context of the compound and not in the context of the radical alone.

The term "residue" with reference to an amino acid or amino acid derivative means a radical derived from the corresponding α-amino acid by eliminating the hydroxyl of the carboxy group and one hydrogen of the α-amino group. For instance, the terms Gln, Ala, Gly, Ile, Arg, Asp, Phe, Ser, Leu, Cys, Asn, Sar and Tyr represent the "residues" of L-glutamine, L-alanine, glycine, L-isoleucine, L-arginine, L-aspartic acid, L-phenylalanine, L-serine, L-leucine, L-cysteine, L-asparagine, sarcosine and L-tyrosine, respectively.

The term "side chain" with reference to an amino acid or amino acid derivative means a residue attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

The term "halo" as used herein means a halo radical selected from bromo, chloro, fluoro or iodo.

The term "lower alkyl" or ($C_{1-6}$ alkyl) as used herein, either alone or in combination with another radical, means straight or branched chain alkyl radicals containing up to six carbon atoms and includes methyl, ethyl, propyl, butyl, hexyl, 1-methylethyl, 1-methylpropyl, 2-methylpropyl and 1,1-dimethylethyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tert-butoxy.

The term "lower alkanoyl" as used herein, either alone or in combination with another radical, means a straight chain 1-oxoalkyl containing from one to six carbon atoms or a branched chain 1-oxoalkyl containing from four to six carbon atoms; for example, acetyl, propionyl(1-oxopropyl), 2-methyl-1-oxopropyl, 2-methylpropionyl and 2-ethylbutyryl.

The term "lower cycloalkyl" as used herein, either alone or in combination with another radical, means saturated cyclic hydrocarbon radicals containing from three to seven carbon atoms and includes cyclopropyl, cyclobutyl, cyclopentyl, cyclohexyl and cycloheptyl.

The term "amino" as used herein means an amino radical of formula $-NH_2$. The term "lower alkylamino" as used herein means alkylamino radicals containing one to six carbon atoms and includes methylamino, propylamino, (1-methylethyl)amino and (2-methylbutyl)amino. The term "di(lower alkyl)amino" means an amino radical having two lower alkyl substituents each of which contains one to six carbon atoms and includes dimethylamino, diethylamino, ethylmethylamino and the like.

The term "Het" as used herein means a monovalent radical derived by removal of a hydrogen from a five- or six-membered saturated or unsaturated heterocycle containing from one to four heteroatoms selected from nitrogen, oxygen and sulfur. Optionally, the heterocycle may bear one or two substituents; for example, N-oxido, lower alkyl, phenyl-($C_{1-3}$)alkyl, lower alkoxy, halo, amino or lower alkylamino. Again optionally, the five- or six-membered heterocycle can be fused to a phenyl. Examples of suitable heterocycles and optionally substituted heterocycles include pyrrolidine, tetrahydrofuran, thiazolidine, pyrrole, 1H-imidazole, 1-methyl-1H-imidazole, pyrazole, furan, thiophene, oxazole, isoxazole, thiazole, 2-methylthiazole, 2-aminothiazole, 2-(methylamino)-thiazole, piperidine, 1-methylpiperidine, 1-methylpiperazine, 1,4-dioxane, morpholine, pyridine, pyridine N-oxide, pyrimidine, 2,4-dihydroxypyrimidine, 2,4-dimethylpyrimidine, 2,6-dimethylpyrimidine, 1-methyl-1H-tetrazole, 2-methyl-2H-tetrazole, benzothiazole and thiazolo[4,5-b]pyridine.

The term "pharmaceutically acceptable carrier" as used herein means a non-toxic, generally inert vehicle for the active ingredient which does not adversely affect the ingredient.

The term "effective amount" means a predetermined antiviral amount of the antiviral agent, i.e. an amount of the agent sufficient to be effective against the virus in vivo.

The azetidin-2-one derivatives of formula 1 can be obtained in the form of therapeutically acceptable acid addition salts. In the instance where a particular derivative has a residue which functions as a base, examples of such salts are those with organic acids, e.g. acetic, lactic, succinic, benzoic, salicylic, methanesulfonic or p-toluenesulfonic acid, as well as polymeric acids such as tannic acid or carboxymethyl cellulose, and salts with inorganic acids such as hydrohalic acids, e.g. hydrochloric acid, or sulfuric acid, or phosphoric acid.

Process

Compounds of formula 1 can be synthesized from commercially available, suitably protected amino acids, as exemplified hereinafter. (For general synthetic procedures see: *The Organic Chemistry of beta-Lactams*, Gunda I. Georg, Ed.; VCH Publishers Inc., New York, N.Y., USA, 1992, pp 1 to 48 and 257 to 293.)

Compounds of formula 1 wherein $R^1$ to $R^5$, inclusive, and Z are as defined herein can be prepared by a process selected from one of the following processes:

A) reacting a key intermediate of formula 2:

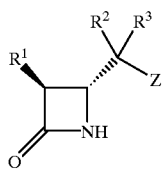

(2)

wherein $R^1$, $R^2$, $R^3$ and Z are as defined herein either (a) with an isocyanate of formula $R^5NCO$ wherein $R^5$ is as defined herein in the presence of a proton acceptor, or (b) with a phenoxycarbamate of formula $R^5NHC(O)OPh$ in the presence of a proton acceptor, to obtain the corresponding compound of formula 1 wherein $R^1$, $R^2$, $R^3$, $R^5$ and Z are as defined herein and $R^4$ is hydrogen; or B) reacting the key intermediate of formula 2 wherein $R^1$ $R^2$, $R^3$ and Z are as defined herein with a carbamoyl chloride derivative of formula $R^4R^5NC(O)Cl$ wherein $R^4$ is lower alkyl, methoxy, ethoxy or benzyloxy, and $R^5$ is as defined herein, or $R^4$ and $R^5$ together with the nitrogen atom to which they are attached form a pyrrolidino, piperidino, morpholino, N-methylpiperazino, 1-(3,4-dihydro-1H-isoquinolinyl or 2-(3,4-dihydro-1H-isoquinolinyl) in the presence of a proton acceptor to obtain the corresponding compound of formula 1 wherein $R^1$, $R^2$, $R^3$ and $R^5$ are as defined herein, and $R^4$ is lower alkyl, methoxy, ethoxy or benzyloxy, or $R^4$ and $R^5$ together with the nitrogen atom to which they are attached are as defined herein, and Z is as defined herein.

The aforementioned key intermediate of formula 2 can be prepared by a process illustrated by Scheme A as follows:

Scheme A

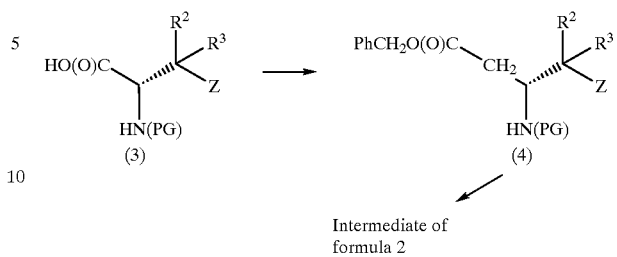

wherein PG is an amino protecting group and $R^2$, $R^3$ and Z are as defined herein.

The starting material of formula 3 is either commercially available or can be made by known methods.

With reference to Scheme A, the protected amino acid (3) is homologized by well known procedures to give the benzyl ester of the corresponding β-amino acid (4). The latter benzyl ester is deprotected to provide the corresponding free amino acid which is cyclodehydrated according to known procedures, see for instance M. F. Loewe et al., Tetrahedron Letters 1991, 32, 2299; and S. Kobayashi et al., J. Am. Chem. Soc., 1981, 103, 2406, to give the key intermediate of formula 2.

The preparation of the compound of formula 1 can be illustrated further by reference to scheme B wherein PG, $R^2$, $R^3$ and $R^5$ are as defined herein and $R^1$, $R^{1A}$ and $R^4$ are as defined hereinbelow in the description of scheme B.

Scheme B

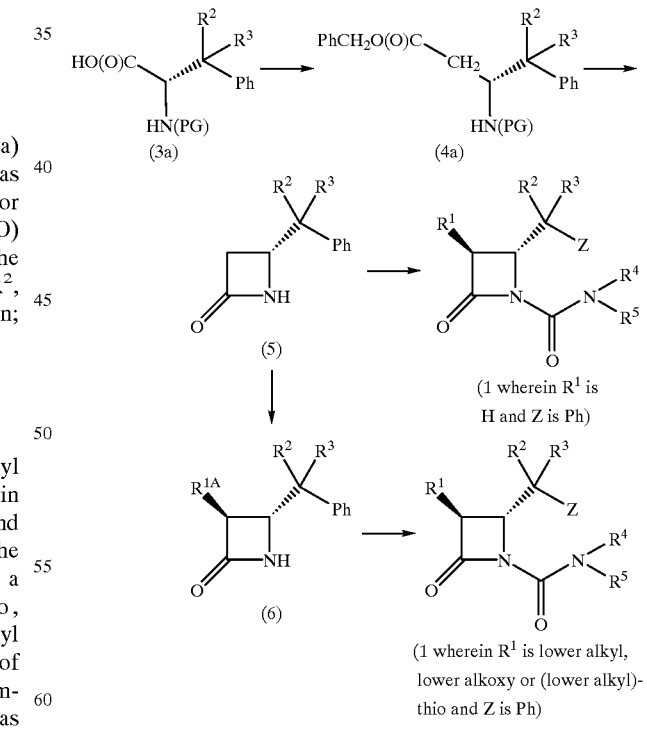

With reference to Scheme B, commercially available, suitably protected amino acid (3a) is homologized by standard procedures to give the benzyl ester of the corresponding β-amino acid (4a). The latter benzyl ester is deprotected to provide the corresponding free amino acid which is cyclodehydrated by known procedures to give a key intermediate of formula 5.

Condensation of the key intermediate (5) with an appropriate isocyanate of formula $R^5NCO$ in the presence of a proton acceptor affords a corresponding ureido derivative which is the compound of formula 1 wherein $R^1$, $R^4$ are hydrogen and $R^2$, $R^3$ and $R^5$ inclusive are as defined herein. Alternatively, a primary or secondary amine, or salts thereof, can be preactivated with triphosgene in presence of a base, for example diisopropylethylamine; or via the formation of the phenoxycarbamate derivative which in turn is reacted with the intermediate of formula 5; to provide the preceding compound of formula 1 wherein $R^1$ is hydrogen.

Optionally, the key intermediate of formula 5 can be functionalized at position 3 of the azetidin-2-one ring; namely, the nitrogen atom of the intermediate of formula 5 is first protected with a suitable N-protecting group and then the resulting N-protected derivative is alkylated by standard methods at position 3. Subsequent deprotection gives the functionalized intermediate (6). Intermediate (6) thereafter can be transformed to the desired ureido compound of formula 1 wherein $R^1$ is lower alkyl, lower alkoxy or (lower alkyl)thio in the same manner as described above for the transformation of key intermediate (5) to the ureido compound of formula 1 wherein $R^1$ is hydrogen and $R^2$ to $R^5$, inclusive, are as defined herein.

The process of this invention can be illustrated further by more specific reference to the process depicted by Scheme B.

Accordingly, an amino protected phenylalanine derivative of formula 3a is homologized to the benzyl ester (4a) according to the following procedure:

(a) reacting an amino protected phenylalanine derivative of formula 3a wherein PG is an amino protecting group and $R^2$ and $R^3$ are as defined herein in the presence of alkyl chloroformate, preferably isobutyl chloroformate, and a tertiary organic base, e.g. N-methylmorpholine or triethylamine, to obtain a corresponding mixed anhydride, (b) reacting the mixed anhydride with diazomethane to obtain a corresponding diazomethylketone, and (c) rearranging the diazomethylketone with silver benzoate in the presence of benzyl alcohol and a tertiary organic base, e.g. N-methylmorpholine or triethylamine, to obtain a corresponding benzyl ester (4a).

Thereafter, benzyl ester (4a) is subjected to deprotection conditions, for instance hydrogenation in the presence of a catalytic amount of palladium hydroxide on carbon when PG is a benzyloxycarbonyl protecting group, to give the corresponding β-amino acid. The latter compound is subjected to cyclodehydration conditions, for instance methanesulfonyl cloride/sodium bicarbonate, in a suitable solvent, e.g. acetonitrile, to give the key intermediate of formula 5 in which $R^2$ and $R^3$ are as defined herein.

The key intermediate of formula 5 can be transformed to the azetidinone derivative of formula 1 wherein $R^1$ and $R^4$ each is hydrogen, $R^2$, $R^3$, $R^5$ are as defined herein and Z is phenyl by reacting the key intermediate of formula 5 with an appropriate isocyanate of formula $R^5NCO$ wherein $R^5$ is as defined herein in the presence of a base (proton acceptor.) A convenient and practical base is triethylamine or preferably lithium bis(trimethylsilyl)amide. In this manner the ureido residue is incorporated into the desired azetidinone (i.e. the compound of formula 1 wherein $R^1$ and $R^4$ each is hydrogen, $R^2$, $R^3$ and $R^5$ are as defined herein and Z is phenyl).

A method for the introduction of the ureido residue so that azetidinone derivatives of formula 1 can be realized for those derivatives in which $R^1$ is hydrogen, $R^2$, $R^3$ and $R^5$ are as defined herein, $R^4$ is lower alkyl, methoxy, ethoxy or benzyloxy, or $R^4$ and $R^5$ together with the nitrogen atom to which they are attached are as defined herein, and Z is phenyl is as follows: reacting the key intermediate (5) with a carbamoyl chloride derivative of formula $R^4R^5NC(O)Cl$ wherein $R^4$ is lower alkyl, methoxy, ethoxy or benzyloxy, and $R^5$ is as defined herein, or $R^4$ and $R^5$ together with the nitrogen atom to which they are attached are as defined herein, in the presence of a suitable tertiary amine, for example diisopropylethylamine or preferably lithium bis(trimethylsilyl)amide. The requisite carbamoyl chloride derivative can be prepared by preactivating the appropriate secondary amine with triphosgene. This particular method for the formation of the ureido residue is especially suitable for the preparation of azetidinone derivatives in which $R^4$ is lower alkyl, and for the preparation of azetidinone derivatives in which $R^4$ and $R^5$ together with the nitrogen atom to which they are attached are as defined herein.

Another method for forming the ureido residue to obtain the desired azetidinone derivatives of formula 1 is which $R^1$ and $R^4$ each is hydrogen, $R^2$, $R^3$ and $R^5$ are as defined herein and Z is phenyl involves reacting the key intermediate (5) with a phenoxycarbamate of formula $R^5HNC(O)OPh$ wherein $R^5$ is as defined herein in the presence of a suitable base (proton acceptor), e.g. triethylamine or preferably lithium bis(trimethylsilyl)amide, thereby obtaining the desired product.

Turning now to the preparation of the azetidinones of formula 1 in which $R^1$ is methyl, ethyl, methoxy or methylthio, $R^2$ to $R^5$, inclusive, are as defined herein and Z is phenyl, the versatile intermediate of formula 5 can be functionalized at position 3 of the azetidinone ring as follows: Firstly a N-protecting group, such as benzyl, (4-methoxyphenyl)methyl or preferably tert-butyldimethylsilanyl ($Me_3C-Si(Me_2)-$), is introduced at position 1 of the intermediate (5). The resulting amino protected derivative of formula 5 then is subjected to standard alkylating conditions with the appropriate electrophilic reagent. More explicitly, enolate formation is effected in the presence of a suitable proton acceptor, e.g. lithium diisopropylamide or lithium bis(trimethylsilyl)amide. Thereafter, the enolate is reacted with (a) a methyl or ethyl halide, e.g. methyl iodide or ethyl iodide; or b) with oxygen in the presence of trimethylphosphite to provide the corresponding 3-hydroxy substituted, which in turn is reacted with diazomethane in the presence of silica gel; or c) with dimethyldisulfide; followed by N-deprotection under standard conditions to give the corresponding functionalized intermediate of formula 6 wherein $R^1$ is methyl or ethyl, or methoxy, or methylthio, respectively, and $R^2$ and $R^3$ are as defined herein.

Thereafter, the functionalized intermediate of formula 6 is converted to the desired compound of formula 1 wherein $R^1$ is methyl, ethyl, methoxy or methylthio, $R^2$ to $R^5$, inclusive, are as defined herein and Z is phenyl in the same manner as described above for the introduction of the ureido residue in the transformation of the key intermediate of formula 5 to the compound of formula 1 in which $R^1$ is hydrogen, $R^2$ to $R^5$, inclusive, are as defined herein and Z is phenyl.

Finally, the preparation the azetidinones of formula 1 wherein $R^2$ and $R^3$ each is hydrogen, $R^1$, $R^4$, $R^5$ are as defined herein and Z is $(CH_2)_p$-(Het) wherein p and Het are as defined herein can be illustrated by Scheme C wherein PG, $R^1$, $R^4$, $R^5$, Het and p are as defined herein:

Scheme C

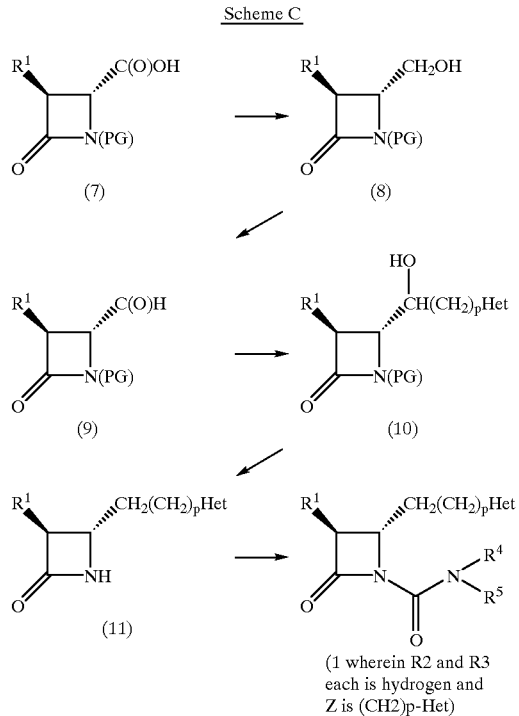

(1 wherein R2 and R3 each is hydrogen and Z is (CH2)p-Het)

With reference to Scheme C, suitably N-protected 4-carboxyazetidinones of formula 7 wherein $R^1$ is as defined herein and PG is an amino protecting group are well known or can be prepared by known methods such as the methods for functionalizing position 3 of azetidinones described hereinbefore. For example, the N-protected 4-carboxyazetidinone of formula 7 wherein PG is the protecting group $Me_3CSi(Me)_2$— has been described by P. E. Finke et al., *J. Med. Chem.* 1995, 38, 2449. The N-protected 4-carboxyazetidinone of formula 7 is reduced to the corresponding 4-(hydroxymethyl)azetidinone derivative of formula 8 with a reducing agent capable of converting an acid to its corresponding alcohol. The 4-(hydroxymethyl) azetidinone is then oxidized to give the aldehyde of formula 9 with a reagent capable of transforming a primary alcohol to its corresponding aldehyde. The latter aldehyde so obtained is reacted with an appropriate Grignard reagent of the formula $Het(CH_2)_p$-(halo)Mg wherein Het and p are as defined herein and halo is bromo, chloro or iodo, or with an appropriate organolithium reagent of the formula $Het(CH_2)_p$—Li to give the product (10). Subsequent removal of the secondary hydroxy group on the side chain at position 4 of product (10) by standard methods, for instance by conversion of the hydroxy moiety to a reducible group which is subsequently removed by reduction, followed by cleavage of the N-protecting group from the resulting protected β-lactam affords the desired intermediate β-lactam of formula 11.

More explicitly, the transformation of the 4-carboxyazetidinone (7) to the desired intermediate (11) can be exemplified as follows: Reduction of the 4-carboxyazetidinone (7) wherein PG is $Me_3CSiMe_2$— and $R^1$ is as defined herein with borane in tetrahydrofuran, or via the formation of a mixed anhydride with isobutyl chloroformate in the presence of an organic tertiary base, e.g. N-methylmorpholine or diisopropylethylamine, followed by reduction of the mixed anhydride with sodium borohydride in water, yields the 4-(hydroxymethyl)azetidinone (8) wherein PG is $Me_3CSiMe_2$— and $R^1$ is as defined herein. The latter compound is oxidized with an appropriate oxidizing agent, e.g. oxalyl chloride-activated dimethyl sulfoxide (K. Omura and D. Swern, *Tetrahedron* 1978, 34, 1651) or triacetoxy periodinane (D. B. Dess and J. C. Martin, *J. Org. Chem.* 1983, 48, 4155) to give the corresponding aldehyde of formula 9. This aldehyde subsequently is reacted with the appropriate Grignard reagent $Het(cH_2)_p$— Mg-(halo) as defined hereinbefore, or with the organolithium reagent $Het(CH_2)_p$—Li as defined hereinbefore to give the addition product (10) as a mixture of diastereoisomers. Deoxygenation of the hydroxy-bearing side chain of addition product (10) can be accomplished in two steps. Firstly, the corresponding diastereoisomeric xanthates can be formed by reacting product (10) with carbon disulfide in the presence of a tertiary amine or with 1,1'-thiocarbonyldiimidazole; the diastereoisomeric xanthates so obtained are reacted with tributyltin hydride in the presence of 2,2'-azobisisobutyronitrile (AIBN) in refluxing benzene. In this manner, deoxygenation of the hydroxy bearing side chain is effected, followed by removal of the N-protecting group to provide the desired intermediate β-lactam of formula 11. The latter intermediate can be transformed into a compound of formula 1 wherein $R^2$ and $R^3$ each is hydrogen, $R^1$, $R^4$ and $R^5$ are as defined herein, and Z is $(CH_2)_p$-Het wherein p and Het are as defined herein in the same manner as described above for the introduction of the ureido residue to the intermediate of formula 5.

More specifically when Het is a tetrazol derivative, intermediate (11) was obtained from derivative (8) using published procedures (J. Fetter; E. Keskeny; T. Czuppon; K. Lempert; M. Kajtar-Peredy; J. Tamas. *J. Chem. Soc. Perkin Trans.* 1992, 1, 3061–3067 and L. T. Giang; J. Fetter; K. Lempert; M. Kajtar-Peredy; A. Gomory; *Tetrahedron*, 1996, 52, 10169–10184).

Antiherpes Activity

The antiherpes activity of the aforementioned azetidinone derivatives of formula 1 (HCMV protease inhibitors) can be demonstrated by biochemical, microbiological and biological procedures.

A biochemical procedure for demonstrating anti-cytomegalovirus activity for the azetidinone derivatives of formula 1 is described in the examples hereinafter. This particular assay determines the ability of a test compound to inhibit the activity of HCMV protease. More specifically, in the assay described herein, the inhibitory activity of the test compound is evaluated on the basis of its ability to interfere with the HCMV No protease cleavage of a fluorogenic peptide substrate which in turn is based on the maturation cleavage site of the enzyme.

Methods for demonstrating the inhibiting effect of the azetidinone derivatives of formula 1 on CMV replication involving cell culture techniques are described in the examples herein.

When the HCMV protease inhibitor is employed as an antiviral agent, it is administered orally, or systemically to humans in a vehicle comprising one or more pharmaceutically acceptable carriers, the proportion of which is determined by the solubility and chemical nature of the compound, chosen route of administration and standard biological practice. For oral administration, the compound or a therapeutically acceptable salt thereof can be formulated in unit dosage forms such as capsules or tablets each containing a predetermined amount of the active ingredient, ranging from about 50 to 500 mg, in a pharmaceutically acceptable carrier.

For parenteral administration, the HCMV protease inhibitor is administered by either intravenous, subcutaneous or intramuscular injection, in compositions with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in standard pharmaceutical texts, e.g. in "Remington's The Science and Practice of Pharmacy", $19^{th}$ ed., Mack Publishing Company, Easton, Pa., 1995, or in "Pharmaceutical Dosage Forms and Drug Delivery Systems", 6th ed., H. C. Ansel et al., Eds., Williams & Wilkins, Baltimore, Md., 1995.

The dosage of the HCMV protease inhibitor will vary with the form of administration and the particular active agent chosen. Furthermore, it will vary with the particular host under treatment. Generally, treatment is initiated with small increments until the optimum effect under the circumstance is reached.

The inhibitor compound is most desirably administered at a concentration level that will generally afford antivirally effective results without causing any harmful or deleterious side effects.

For oral administration, the HCMV protease inhibitor is administered in the range of 20 to 200 mg per kilogram of body weight per day, with a preferred range of 25 to 100 mg per kilogram.

For ocular administration, the HCMV protease inhibitor is administered either topically or intraocularly (injection or implant) in a suitable preparation. For example, an implant containing the compound in a suitable formulation can be surgically plated in the posterior segment of the eye through a small incision.

With reference to systemic administration, the HCMV protease inhibitor is administered at a dosage of 10 mg to 150 mg per kilogram of body weight per day, although the aforementioned variations will occur. However, a dosage level that is in the range of from about 10 mg to 100 mg per kilogram of body weight per day is most desirably employed in order to achieve effective results.

EXAMPLES

The following examples further illustrate this invention. All reactions were performed under nitrogen or argon atmosphere unless stated otherwise. Temperatures are given in degrees Celsius. Solution percentages or ratios express a volume to volume relationship, unless stated otherwise. Nuclear magnetic resonance spectra were recorded on a Bruker 400 MHz spectrometer; the chemical shifts ($\delta$) are reported in parts per million. Abbreviations or symbols used herein include Abz: 2-aminobenzoic acid; Bzl: benzyl (also known as phenylmethyl); DIEA: diisopropylethylamine; DMF: dimethylformamide; DMSO: dimethylsulfoxide; EDTA: ethylenediaminetetracetic acid; Et: ethyl; EtOAc: ethyl acetate; $Et_2O$: diethyl ether; HRMS: high resolution mass spectrometry; MS(ES): electrospray mass spectrometry; MS(FAB) or FAB/MS: fast atom bombardment mass spectrometry; FBS: fetal bovine serum; Me: methyl; MeOH: methanol; MeCN: acetonitrile; PFU: plaque forming units; Ph: phenyl; THF: tetrahydrofuran.

Example 1

4(S)-Benzyl-3(S)-methyl-2-oxoazetidine-1-carboxylic acid benzylamide (1: $R^1$=Me, $R^2$, $R^3$ and $R^4$ each=H, $R^5$=Bzl and Z=Ph) (Table 2, entry #207).

Step A

To a solution of N-(benzyloxycarbonyl-L-phenylalanine (18.7 g, 62 mmol) in THF (300 mL) was added $Et_3N$ (6.9 g, 9.5 mL, 68 mmol). The mixture was cooled to −10°. Isobutylchloroformate (11.0 g, 10.5 mL, 81 mmol) was added dropwise over 10 min. After 30 min at −10°, and 30 min at room temperature (20–22°), a solution of diazomethane in $Et_2O$ (0.3–0.5 M, 500 mL) was added. The reaction mixture was stirred for 10 min and then purged with nitrogen for 2 h. The resulting white precipitate was removed by filtration and the filtrate was concentrated under reduced pressure. The residue was purified by flash chromatography ($SiO_2$, 20% EtOAc in hexane) to give 15.9 g (83% yield) of the desired diazoketone as a yellow solid.

The diazoketone (13.2 g, 43 mmol) was dissolved in THF (150 mL). Benzyl alcohol (4.66 mL, 45 mmol) was added at room temperature. Silver benzoate (977 mg, 4.29 mmol) in triethylamine (8.92 mL, 64 mmol) was added dropwise (vigorous gas evolution). After 30 min at room temperature, the reaction mixture was concentrated under reduced pressure. The residue was dissolved in EtOAc. The solution was washed with $H_2O$ and brine, dried ($MgSO_4$) and concentrated. The residue was purified by flash chromatography ($SiO_2$, 15% EtOAc in hexane) to yield 3(S)-{{(benzyloxy)carbonyl}amino}-4-phenylbutyric acid benzyl ester (11 g, 63% yield) as a white solid. $^1$H-NMR (400 MHz, $CDCl_3$) $\delta$7.40–7.10 (m, 15H), 5.27 (brd, J=8.0 Hz, 1H), 5.14 (d, J=12.2 Hz, 1H), 5.10 (d, J=12.2 Hz, 1H), 5.06 (s, 2H), 4.30–4.20 (m, 1H), 2.93 (dd, J=13.3, 6.5 Hz, 1H), 2.82 (dd, J=13.3, 7.6 Hz, 1H), 2.57 (dd, J=16, 5.5 Hz, 1H), 2.50 (dd, J=16, 5.0 Hz, 1H).

Step B

The 3(S)-{{(benzyloxy)carbonyl}amino}-4-phenylbutyric acid benzyl ester (from step A) (10.97 g, 27.2 mmol) in MeOH (1 L) was stirred at room temperature for 7 h under an hydrogen atmosphere (1 atmosphere) in the presence of 20% Pd $(OH)_2$/C (50 mg). The catalyst was removed by filtration through diatomaceous earth. The filtrate was concentrated under reduced pressure to yield 4.53 g (93% yield) of 3(S)-amino-4-phenylbutyric acid as a white solid. A suspension of $NaHCO_3$ (12.74 g, 152 mmol) in MeCN (1.55 L) was stirred and heated to gentle reflux. Mesyl chloride (2.15 mL, 27.8 mmol) was added, followed by the portionwise addition of the preceding acid (4.53 g, 25.3 mmol) over 5 h. After 16 h under reflux, the solid was removed by filtration at 60° and the filtrate was concentrated under reduced pressure. The residual solid was triturated with EtOAc and filtered. The filtrate was concentrated and the residue purified by flash chromatography ($SiO_2$, 40% EtOAc in hexane) to give 4(S)-benzylazetidin-2-one (2.20 g, 54% yield) as a white solid. $^1$H-NMR (400 MHz, $CDCl_3$) $\delta$7.35–7.17 (m, 5H), 5.83 (brs, 1H), 3.88–3.82 (m, 1H), 3.08 (ddd, J=14.8, 5.0, 2.2 Hz, 1H), 2.98 (dd, J=13.7, 5.7 Hz, 1H), 2.84 (dd, J=13.7, 7.9 Hz, 1H), 2.70 (ddd, J=14.9, 2.0, 1.3 Hz, 1H).

Step C

To a solution of 4(S)-benzylazetidin-2-one (400 mg, 2.48 mmol) in $CH_2Cl_2$ (8 mL) was added DIEA (648 μL, 3.72 mmol), followed by tert-butyldimethylsilyl chloride (411 mg, 2.73 mmol). The reaction mixture was stirred for 16 h at room temperature. The $CH_2Cl_2$ was evaporated and the residue was purified by flash chromatography ($SiO_2$, 12%

EtOAc in hexane) to give 4(S)-benzyl-1-(tert-butyldimethylsilyl)azetidin-2-one (647 mg, 95% yield) as a white solid. $^1$H-NMR (400 MHz, CDCl$_3$) δ7.34–7.15 (m, 5H), 3.77–3.70 (m, 1H), 3.25 (dd, J=13.5, 3.5 Hz, 1H), 2.99 (dd, J=15.5 Hz, 5 Hz, 1H), 2.70 (dd, J=15.5, 2.5 Hz, 1H), 2.59 (dd, J=13.5, 11 Hz, 1H), 1.01 (s, 9H), 0.31 (s, 3H), 0.29 (s, 3H).

Step D

To a solution of diisopropylamine (705 μL, 5.03 mmol) in anhydrous THF (12 mL) at −20° was added butyllithium (2.87 mL, 4.60 mmol, 1.6 M in hexane). After the reaction mixture was cooled to −78°, a solution of 4(S)-benzyl-1-(tert-butyldimethyl-silyl)azetidin-2-one (640 mg, 2.32 mmol) in THF (4 mL) was added and the mixture was stirred at −78° for 15 min followed by addition of methyl iodide (488 mg, 214 μL, 3.44 mmol). After 10 min, the reaction mixture was poured into EtOAc (125 mL). The organic phase was washed with aqueous NaHSO$_4$ (1M) and brine, dried (MgSO$_4$), filtered and concentrated. The residual oil was purified by flash chromatography (SiO$_2$, 6% EtOAc in hexane) to give 4(S)-benzyl-1-(tert-butyldimethylsilyl)-3(S)-methylazetidin-2-one (557 mg, 83% yield) as a pale yellow solid. $^1$H-NMR (400 MHz, CDCl$_3$) δ7.33–7.15 (m, 5H), 3.35 (ddd, J=10.8, 3.8, 2.5 Hz, 1H), 3.21 (dd, J=13.4, 3.8 Hz, 1H), 2.88 (qd, J=7.5, 2.5 Hz, 1H), 2.60 (dd, J=13.4, 10.8 Hz, 1H), 1.02 (d, J=7.5 Hz, 3H), 1.00 (s, 9H), 0.31 (s, 3H), 0.27 (s, 3H).

Step E

To a solution of 4(S)-benzyl-1-(tert-butyldimethyl-silyl)-3(S)-methylazetidin-2-one (557 mg, 1.92 mmol) in MeOH (25 mL) at 0° was added cesium fluoride (439 mg, 2.89 mmol). After 1 h MeOH was evaporated under reduced pressure and the residue was dissolved in EtOAc. The organic phase was washed with H$_2$O and brine, dried (MgSO$_4$), filtered and concentrated. The residue was purified by flash chromatography (SiO$_2$, 50% EtOAc in hexane) to give 4(S)-benzyl-3(S)-methylazetidin-2-one (239 mg, 71% yield) as a white solid. $^1$H-NMR (400 MHz, CDCl$_3$) δ7.35–7.17 (m, 5H), 5.78 (brs, 1H), 3.46 (ddd, J=8.0, 5.9, 2.0 Hz, 1H), 2.98 (dd, J=13.5, 5.9 Hz, 1H), 2.91 (qd, J=7.3, 2.0 Hz, 1H), 2.84 (dd, J=13.5, 8.0 Hz, 1H), 1.26 (d, J=7.3 Hz, 3H).

Step F

To a solution of 4(S)-benzyl-3(S)-methylazetidin-2-one (50 mg, 0.28 mmol) in THF (4 mL) at −78°, lithium bis(trimethylsilyl)amide (280 μL, 280 mmol, 1 M in THF) was added. After 10 min, benzyl isocyanate (37.2 mg, 34.6 μL, 0.28 mmol) was added. Stirring was continued at −78° for 45 min. The reaction mixture was diluted with EtOAc (50 mL) and washed with aqueous NaHSO$_4$ (1M) and brine, dried (MgSO$_4$), filtered and concentrated. The residue was purified by flash chromatography (SiO$_2$, 14% EtOAc in hexane) to give the title compound 4(S)-benzyl-3(S)-methyl-2-oxoazetidine-1-carboxylic acid benzylamide (23 mg, 27% yield) as a colorless oil. $^1$H-NMR (400 MHz, CDCl$_3$) δ7.38–7.19 (m, 10H), 6.94 (t, J=5.1 Hz, 1H), 4.53 (dd, J=14.9, 6.0 Hz, 1 H), 4.48 (dd, J=14.9, 6.0 Hz, 1H), 3.90 (ddd, J=8.6, 3.2, 2.9 Hz, 1H), 3.53 (dd, J=13.7, 3.5 Hz, 1 H), 2.95 (qd, J=7.6, 2.5 Hz, 1H), 2.92 (dd, J=13.3, 8.9 Hz, 1H), 1.14 (d, J=7.6 Hz, 3H); FAB MS m/z 309.3 (MH$^+$); HRMS calcd for C$_{19}$H$_{21}$N$_2$O$_2$: 309.1603 (MH$^+$); found: 309.1614.

Example 2

4(S)-Benzyl-2-oxoazetidine-1-carboxylic acid benzyl-amide (1: R$^1$, R$^2$, R$^3$ and R$^4$ each=H, R$^5$= Bzl and Z=Ph) (Table 1, entry #116).

By following the procedure of step F of example 1, but replacing 4(S)-benzyl-3(S)-methylazetidin-2-one with an equivalent amount of 4(S)-benzylazetidin-2-one, described in step B of example 1, the title compound was obtained. $^1$H-NMR (400 MHz, CDCl$_3$) δ7.46 (t, J=6.4 Hz, 1H), 7.36–7.21 (m, 10H), 4.36 (d, J=6.4 Hz, 2H), 4.21 (m, 1H), 3.27 (dd, J=11.8, 3.8 Hz, 1H), 3.06 (dd, J=15.8, 5.6 Hz, 1H), 2.93 (dd, J=11.8, 8.9 Hz, 1H), 2.73 (dd, J=15.8, 3.0 Hz, 1H); IR (CDCl$_3$) υ1769, 1700 cm$^{-1}$; FAB MS m/z 295.2 (MH$^+$); HRMS calcd for C$_{18}$H$_{19}$N$_2$O$_2$: 295.1447 (MH$^+$); found: 295.1452.

Example 3

1(R)-Phenylpropyl isocyanate (Intermediate for introducing the 1(R)-phenylpropyl group at R$^5$ of the compound of formula 1)

To a solution of 1(R)-phenylpropylamine (14.33 g, 106 mmol) in Et$_2$O (102 mL) was added a 1.0 M solution of HCl/Et$_2$O (212 mL, 212 mmol). The resulting solution was stirred for 30 min and then evaporated to dryness on a rotary evaporator. The resulting white hydrochloride salt was suspended in toluene (200 mL). Triphosgene was added (11.67 g, 39.3 mmol) and the resulting suspension was stirred at reflux for 3 h and at room temperature for 18 h. The reaction mixture was concentrated and the final volume adjusted to 200 mL with toluene giving a final concentration of 0.53M. The resulting isocyanate solution was used as such. An aliquot (170 mL) was concentrated to give a colorless oil: $^1$H-NMR (400 MHz, CDCl$_3$) δ7.36–7.22 (m, 5H), 4.50 (t, J=6.7 Hz, 1H), 1.82 (q, J=7.3 Hz, 2H), 0.94 (t, J=7.3 Hz, 2H).

Example 4

4-{{(Phenoxycarbonyl)amino}methyl}pyridine (Intermediate for introducing the 4-(aminomethyl) pyridinyl group at R$^5$ of the compound of formula 1)

To a solution of 4-(aminomethyl)pyridine (10.7 g, 98.5 mmol) in CH$_2$Cl$_2$ (245 mL) at 0°, was added Et$_3$N (14.2 mL, 19.9 g, 197 mmol), followed by a dropwise addition of phenylchloroformate (14.8 mL, 18.5 g, 118 mmol). After stirring for 1 h, the resulting mixture was diluted with EtOAc (1.5 L). The organic phase was washed twice with water, then brine, dried over sodium sulfate and concentrated under reduced pressure. Purification of the residue by chromatography (SiO$_2$, gradient EtOAc to 10% MeOH/CHCl$_3$) gave a yellow solid which was recrystallized from EtOAc:hexane (2:1) to yield the desired compound (9.55 g, 41.85 mmol, 42% yield). $^1$H-NMR (400 MHz, CDCl$_3$) δ8.61 (d, J=5.7 Hz, 2H), 7.40–7.15 (m, 7H), 5.61 (bs, 1H), 4.50 (d, J=6.4 Hz, 2H).

Example 5

N-Methyl-N-{{4-(trifluoromethyl) phenyl}methyl}carbamoyl chloride (Intermediate for introducing methyl at R$^4$ and {4-(trifluoromethyl)phenyl}methyl at R$^5$ of the compound of formula 1)

To a solution of {4-(trifluoromethyl)phenyl}methyl bromide (20.0 g, 83.7 mmol) in EtOH was added methylamine (100 mL of 40% aqueous solution, 1290 mmol). After 2 h, the reaction was concentrated under reduced pressure. The aqueous phase was separated and extracted with EtOAc (2×100 mL). The combined organic phase was washed with 5% aqueous NaHCO$_3$ solution and then brine, dried over magnesium sulfate, filtered and evaporated to dryness. The resulting residue was dissolved in HCl/dioxane (4N, 100 mL). The solvent was removed under reduced pressure. The resulting solid was triturated with Et$_2$O and collected by suction filtration to provide N-methyl {4-(trifluoromethyl) phenyl}methylamine hydrochloride salt (17.0 g, 90% yield) as a white solid. The salt was suspended in CH$_2$Cl$_2$ (150 mL), and the suspension was cooled at 0°. DIEA (30.2 mL, 173 mmol) was added to the cooled solution, followed by the addition of a phosgene solution in toluene (1.93 M, 55 mL, 105.7 mmol). After 2 h at 0°, the reaction mixture was concentrated and the resulting thick gum was extracted with Et$_2$O. Evaporation of the Et$_2$O extract gave a light yellow oil which was purified by flash chromatography (SiO$_2$: 10% EtOAc in hexane) to give the title compound as a pale yellow oil (16.0 g, 84% yield). $^1$H-NMR (400 MHz, CDCl$_3$) δ7.59 (m, 2H), 7.33 (m, 2H), 4.72 and 4.58 (2×s, 2H), 3.04 and 2.97 (2×s, 3H).

Example 6

4(S)-tert-Butyl-2-oxoazetidine-1-carboxylic acid (1 (R)-phenylpropyl)amide (1: R$_1$=H, R$_2$=R$_3$=Z=Me, R$_4$=H, R$_5$=1-(R)Ph-Pr) (Table 2, entry #215)

By following the same procedure as in example 1, step A, but using 2(S)-{(benzyloxycarbonyl)amino}-3,3-dimethylbutanoic acid as the starting material, 3(S)-{(benzyloxycarbonyl)amino}-4,4-dimethylpentanoic acid benzyl ester is obtained as a colorless oil. $^1$H-NMR (400 MHz, CDCl$_3$) δ7.28–7.19 (m, 10H), 5.01–4.93 (m, 4H), 4.80 (d, J=10.2 Hz, 1H), 3.94 (td, J=9.9, 3.8 Hz, 1H), 2.59 (dd, J=14.6, 4.1 Hz, 1H), 2.24 (dd, J=14.3, 9.9 Hz, 1H), 0.85 (s, 9H)

Step B

The 3(S)-{(benzyloxycarbonyl)amino}-4,4-dimethylpentanoic acid benzyl ester (from step A) (490 mg, 1.33 mmol) in EtOH (13.3 mL) was stirred at room temperature for 16 h under an hydrogen atmosphere (1 atmosphere) in the presence of 20% Pd(OH)$_2$/C (50 mg). The catalyst was removed by filtration over diatomaceous earth. The filtrate was concentrated under reduced pressure to yield 186 mg (96% yield) of the expected amino acid as a white solid.

To a suspension of the amino acid (169 mg, 1.16 mmol) in MeCN (116 mL) and H$_2$O (20 drops) was added 2-chloro-1-methylpyridinium iodide (356 mg, 1.39 mmol), followed by Et$_3$N (405 μL, 2.90 mmol). The resulting yellow suspension was stirred for 6 h at reflux, and then at room temperature for 18 h. The mixture was concentrated to dryness and the residue was purified by flash chromatography (SiO$_2$, 75% EtOAc in hexane) to yield 4(S)-tert-butylazetidine-2-one (93 mg, 63% yield) as a white solid. $^1$H-NMR (400 MHz, CDCl3) δ5.83–5.67 (bs, 1H), 3.45 (dd, J=5.1, 2.6 Hz, 1H), 2.85 (ddd, J=14.9, 5.1, 2.5 Hz, 1H), 2.69 (ddd, J=14.9, 2.5, 1.0 Hz, 1H), 0.93 (s, 9H).

Step C

Following the same procedure as in example 1, step F, but using 4(S)-tert-butylazetidine-2-one as starting material and 1(R)-phenylpropyl isocyanate as reactant, 4(S)-tert-butyl-2-oxoazetidine-1-carboxylic acid (1(R)-phenylpropyl)amide was obtained as a waxy solid.

$^1$H-NMR (400 MHz, CDCl$_3$) δ7.35–7.24 (m, 5H), 7.21 (d, J=10.2 Hz, 1H), 4.76 (dd, J=15.3, 7.6 Hz, 1H), 3.91 (dd, J=6.0, 3.9 Hz, 1H), 2.96 (dd, J=16.2, 6.0 Hz, 1H), 2.76 (dd, J=16.2, 3.2 Hz, 1H), 1.91–1.79 (m, 2H), 1.03 (s, 9H), 0.93 (t, J=7.3 Hz, 3H); IR (CHCl$_3$) υ3361, 1752, 1693 cm$^{-1}$; FAB MS m/z 289.1 (MH$^+$); HRMS calcd for C$_{17}$H$_{25}$N$_2$O$_2$: 289.1916 (MH$^+$); found: 289.1921.

Example 7

4(S)-Benzyl-2-oxoazetidine-1-carboxylic acid N-methyl-N-{{4-(trifluoromethyl) phenyl}methyl}amide (1: R$_1$=R$_2$=R$_3$=H, R$_4$=Me, R$_5$=CH$_2$(4-CF$_3$)-Ph, Z=Ph) (Table 1, entry #135).

To a solution of 4(S)-benzyl-azetidin-2-one (110 mg, 0.68 mmol) (from example 1, step B) in THF (6 mL) at −50°, potassium bis(trimethylsilyl)amide (1.43 mL, 0.717 mmol, 0.5 M in toluene) was added. After 20 min the reaction mixture was added via cannula to a solution of N-methyl-N-{{4-(trifluoromethyl)phenyl}carbamoyl chloride (from example 5) (860 mg, 3.4 mmol) in THF (6 mL). The reaction mixture was stirred for 2 h during which time the temperature rose to −20°. The reaction was then quenched with brine (2 mL) and diluted with EtOAc (25 mL). The aqueous phase was extracted with EtOAc (2×10 mL). The combined organic layers were washed with brine, dried (MgSO$_4$), filtered and concentrated. The residue was purified by flash chromatography (SiO$_2$, 20% EtOAc in hexane) to give the title compound (102 mg, 40% yield) as a colorless oil. $^1$H-NMR (400 MHz, CDCl$_3$) δ7.58 (d, J=7.9 Hz, 2H), 7.31 (d, J=7.9 Hz, 2H), 7.26–7.10 (m, 5H), 4.80–4.53 (m, 2H), 4.41 (m, 1H), 3.15 (dd, J=14.8, 3.8 Hz, 1H), 2.85 (s, 3H), 2.84 (m, 2H), 2.65 (dd, J=14.8, 3.5 Hz, 1H); IR (neat) υ1778, 1665 cm$^{-1}$, FAB MS m/z 377 (MH$^+$); HRMS calcd for C$_{20}$H$_{20}$F$_3$N$_2$O$_2$: 377.1477; found: 377.1488.

Example 8

4(S)-Benzyl-2-oxoazetidine-1-carboxylic acid (4-pyridinylmethyl) amide (1: R$_1$=R$_2$=R$_3$=R$_4$=H, R$_5$=CH$_2$-(4-Py), Z=Ph) (Table 1, entry #136).

Following the same procedure as in example 1, step F, but using 4-{{(phenoxycarbonyl)amino}methyl}pyridine (from example 4) as reactant instead of benzyl isocyanate, the title compound is obtained as a white solid. $^1$H-NMR (400 MHz, CDCl$_3$) δ8.55 (m, 2H), 7.38–7.12 (m, 7H), 7.01 (m,1H), 4.47 (m, 2H), 4.29 (m, 1H), 3.41 (dd, J=14.0, 3.0 Hz, 1H), 2.99 (dd, J=16.2, 5.8 Hz, 1H), 2.93 (dd, J=14.0, 8.4 Hz, 1H), 2.73 (dd, J=16.2, 2.9 Hz, 1H); IR (CDCl$_3$) υ3357, 1764, 1694 cm$^{-1}$, FAB MS m/z 296.1 (MH$^+$); HRMS calcd for C$_{17}$H$_{18}$N$_3$O$_2$: 296.1399; found: 296.1408.

Example 9

4(S)-Benzyl-3(S)-(methylthio)-2-oxoazetidine-1-carboxylic acid (1(R)-phenylpropyl)amide (1: R$_1$=MeS, R$_2$=R$_3$=R$_4$=H, R$_5$=1(R)Ph-Pr, Z=Ph) (Table 2, entry #209).

Following the same procedure as in example 1, step D, but replacing methyliodide with dimethyl disulfide, 4(S)-benzyl-1-(tert-butyldimethylsilyl)-3(S)-(methylthio) azetidin-2-one is obtained. $^1$H-NMR (400 MHz, CDCl$_3$) δ7.36–7.20 (m, 5H), 3.75 (d, J=2.6 Hz, 1H), 3.66 (ddd, J=10.5, 3.8, 2.2 Hz, 1H), 3.29 (dd, J=13.7, 3.8, 1H), 2.67 (dd, J=13.7, 10.5 Hz, 1H), 1.82 (s, 3H), 1.03 (s, 9H), 0.34 (s, 3H), 0.31 (s, 3H).

Following the deprotection procedure described in example 1, step E, but using 4(S)-benzyl-1-(tert-butyldimethylsilyl)-3(S)-(methylthio)azetidin-2-one as the starting material, followed by urea formation as shown in example 1, step F, but using 1(R)-phenylpropyl isocyanate (from example 3) as reactant, the title compound is obtained as a colorless oil. $^1$H-NMR (400 MHz, CDCl$_3$) δ7.38–7.21 (m, 10H), 6.90 (d, J=8.6 Hz, 1H), 4.82 (dd, J=15.4, 7.5 Hz, 1H), 4.13 (ddd, J=8.3, 2.5, 2.5 Hz, 1H), 3.77 (d, J=2.5 Hz, 1H), 3.49 (dd, J=14.3, 3.5 Hz, 1H), 3.08 (dd, J=14.3, 8.3 Hz, 1H), 1.93 (s, 3H), 1.93–1.84 (m, 2H), 0.96 (t, J=7.3 Hz, 3H); IR (CHCl$_3$) υ3359, 1763, 1702 cm$^{-1}$; FAB MS m/z 369.2 (MH$^+$); HRMS calcd for C$_{21}$H$_{25}$N$_2$O$_2$S: 369.1637 (MH$^+$); found: 369.1646.

Example 10

4(S)-Benzyl-3(S)-methoxy-2-oxoazetidine-1-carboxylic acid (4-pyridinylmethyl)amide (1: R$_1$=MeO, R$_2$=R$_3$=R$_4$=H, R$_5$=CH$_2$-(4-Py) (Table 2, entry #210).

To a solution of diisopropylamine (800 μL, 5.7 mmol) in anhydrous THF (40 mL) at −20° was added butyllithium (3.56 mL, 5.7 mmol, 1.6 M in hexane). After 15 min., the reaction was cooled to −78°, and freshly distilled trimethylphosphite (1.12 mL, 7.6 mmol) was added followed by a solution of 4(S)-benzyl-1-(tert-butyldimethylsilyl)azetidin-2-one (from example 1, step C, 1.05 g, 3.8 mmol) in THF (10 mL). A constant stream of oxygen was introduced and the mixture was stirred at −78° for 3 h. The reaction mixture was quenched with saturated aqueous NH$_4$Cl and extracted with EtOAc (120 mL). The organic layer was washed with brine, dried (MgSO$_4$), filtered and concentrated. The residue was purified by flash chromatography (SiO$_2$, 10% EtOAc-hexane to 30% EtOAc in hexane) to give 4(S)-benzyl-1-(tert-butyldimethylsilyl)-3(S)-hydroxyazetidin-2-one (671 mg , 60% yield) as a white solid. $^1$H-NMR (400 MHz, CDCl$_3$) δ7.25–7.21 (m, 5H), 4.51 (d, J=2 Hz, 1H), 3.75–3.71 (m, 1H), 3.26 (bs, 1H), 3.20 (dd, J=14, 3.8 Hz, 1H), 2.66 (dd, J=14, 11.1 Hz, 1H), 1.00 (s, 9H), 0.30 (d, J=3.5 Hz, 6H).

To a solution of 4(S)-benzyl-1-(tert-butyldimethyl-silyl)-3(S)-hydroxyazetidin-2-one (150 mg, 0.51 mmol) in Et$_2$O (70 mL) at 0° was added silica gel (40–60 μm, 9 g). The vigorously stirred mixture was treated with diazomethane in Et$_2$O (50 mL, 0.3–0.5 M solution). Once the yellow color had almost disappeared after about 15 min, additional diazomethane solution (20 mL) was added. This procedure was repeated several times until no more starting material could be detected on TLC (about 1.5 h). The reaction mixture was stirred for an additional hour at room temperature then filtered and concentrated to give 4(S)-benzyl-1-(tert-butyl-dimethylsilyl)-3(S)-methoxyazetidin-2-one (157 mg, 99% yield) as a white solid which was pure enough for further manipulation. $^1$H-NMR (400 MHz, CDCl$_3$) δ7.27–7.20 (m, 5H), 4.16 (d, J=1.9 HZ, 1H), 3.67 (ddd, J=11.1, 3.8, 1.9 Hz, 1H), 3.23 (dd, J=13.5, 3.8 Hz, 1H), 2.94 (s, 3H), 2.57 (dd, J=13.4, 11.1 Hz, 1H), 1.01 (s, 9H), 0.32 (d, J=6 Hz, 6H).

Following the same procedure as in example 1 step E, but using 4(S)-benzyl-1-(tert-butyldimethylsilyl)-3(S)-methoxyazetidin-2-one as the starting material, 4(S)-benzyl-3(S)-methoxyazetidin-2-one was obtained. $^1$H-NMR (400 MHz, CDCl$_3$) δ7.36–7.18 (m, 5H), 6.00 (brs, 1H), 4.26 (t, J=1.9 Hz, 1H), 3.80 (ddd, J=7.8, 6.2, 1.6 Hz, 1H), 3.34 (s, 3H), 2.98 (dd, J=14, 6.2 Hz, 1H), 2.88 (dd, J=14, 7.8 Hz, 1H).

Following the same procedure as in example 1 step F, but using 4(S)-benzyl-3(S)-methoxyazetidin-2-one as starting material and 4-{{(phenoxycarbonyl)amino}methyl}pyridine as reactant, 4(S)-benzyl-3(S)-methoxy-2-oxoazetidine-1-carboxylic acid (4-pyridinylmethyl)amide was obtained as a light yellow oil. $^1$H-NMR (400 MHz, CDCl$_3$) δ8.60–7.22 (m, 9H), 7.06–7.04 (m, 1H), 4.52–4.50 (m, 2H), 4.28 (d, J=2.2 Hz, 1H), 4.21–4.17 (m, 1H), 3.57 (dd, J=14, 3.5 Hz, 1H), 3.15 (s, 3H), 2.93 (dd, J=14.2, 8.9 Hz, 1H); IR (neat) υ1773,1770 cm$^{-1}$; FAB-MS m/z 329 (MH$^+$); HRMS calcd for C$_{18}$H$_{20}$N$_3$O$_3$: 326.1504 (MH$^+$); found: 326.1519.

Example 11

4(R)-(2-Thiazolylmethyl)-2-oxoazetidine-1-carboxylic acid N-methyl-N-{{(4-trifluoromethyl)phenyl}methyl}amide (1: R$_1$=R$_2$=R$_3$=H, R$_4$=Me, R$_5$=CH$_2$-(4-CF$_3$-Ph), Z=2-thioazolyl) (Table 2, entry 218).

To a solution of 1-(tert-butyldimethylsilyl)-4-oxoazetidine-2(R)-carboxylic acid (15.0 g, 65.40 mmol) in THF (367 mL) at 0°, was added N-methylmorpholine (7.2 mL, 65.40 mmol) and isobutyl chloroformate (8.5 mL, 65.40 mmol). After stirring for 1.5 h at 0° a solution of NaBH$_4$ (9.9 g, 261.61 mmol) in H$_2$O (98 mL) was added portionwise. The reaction was stirred for 45 min, then diluted with EtOAc and quenched with aqueous HCl solution (10%) to pH 5–6. The organic phase was collected and the aqueous phase was extracted twice with EtOAc. The combined organic layers were washed with saturated aqueous NaHCO$_3$ and brine, dried (MgSO$_4$), filtered and concentrated. The residual oil was purified by flash chromatography (SiO$_2$, eluent:gradient 25% to 50% EtOAc/hexane) to provide 1-(tert-butyldimethylsilyl)-4(R)-(hydroxymethyl)azetidin-2-one (8.46 g, 60% yield) as a white solid. $^1$H-NMR (400 MHz, CDCl$_3$) δ3.74–3.69 (m, 1H), 3.65–3.56 (m, 2H), 3.1–2.98 (m, 1H), 2.81–2.76 (m, 1H), 2.01 (s, 1H), 0.89 (s, 9H), 0.18 (s, 3H), 0.16 (s, 3H). FAB MS m/z 216.2 (MH$^+$).

A solution of 1-(tert-butyldimethylsilyl)-4(R)-(hydroxymethyl)azetidin-2-one (309 mg, 1.44 mmol) and Dess-Martin periodinane (917 mg, 2.16 mmol) in CH$_2$Cl$_2$ (15 mL) was stirred at room temperature for 1 h. A 1:1 mixture of 10% aqueous NaHSO$_3$:saturated aqueous solution of NaHCO$_3$ (20 mL) was added and the mixture was stirred vigorously until both layers were clear (15 min). The mixture was then extracted with Et$_2$O, washed with NaHCO$_3$ and brine, dried (MgSO$_4$), filtered and concentrated. The resulting aldehyde (263 mg, 85% yield) was immediately dissolved in THF (5 mL) and added dropwise to a solution of 2-lithiothiazole [prepared by the addition of butyllithium (1.3 mmol, 1.04 mL, 1.25 M) to a solution of thiazole (1.3 mmol, 115 mg) in THF (15 mL) at −50°]. The resulting solution was stirred at −50° for 45 min then quenched with a saturated aqueous solution of NH$_4$Cl. The mixture was extracted with EtOAc. The extract was washed with brine, dried (MgSO$_4$), filtered and concentrated. The resulting residue was purified by radial chromatography (40% EtOAc in hexane) to afford the desired mixture of diastereoisomeric alcohols. $^1$H-NMR (400 MHz, CDCl$_3$) δ7.73 (d, J=3.2 Hz, 1H), 7.34 (d, J=3.2 Hz, 1H), 4.98 (d, J=6.7 Hz, 1H), 4.20 (brs, 1H), 3.93–3.89 (m, 1H), 3.01 (dd, J=15.7, 5.7 Hz, 1H), 2.77 (dd, J=15.7, 2.8 Hz, 1H), 0.99 (s, 9H), 0.30 (s, 3H), 0.24 (s, 3H).

A solution of the diastereoisomeric alcohols (121 mg, 0.41 mmol) and 1,1'-thiocarbonyldiimidazole (216 mg, 1.22 mmol) in CH$_2$Cl$_2$ was stirred at room temperature for two days. The resulting mixture was then evaporated and subjected to flash chromatography (SiO$_2$, 40% EtOAc in hexane) to afford the desired mixture of diastereoisomeric xanthates (127 mg, 77% yield). $^1$H-NMR (400 MHz, CDCl$_3$) δ8.40–8.35 (m, 1H), 7.87–7.84 (m, 1H), 7.66–7.58 (m, 1H), 7.44–7.40 (m, 1H), 7.10–7.07 (m, 1H), 6.90–6.85 (m, 1H), 6.90–6.85 (m, 1H), 4.47–4.43 and 4.35–4.33 (2×m, 1H), 3.22 (dd, J=15.8, 5.8 Hz, 1H), 3.02 (dd, J=15.8, 2.7 Hz, 1H), 0.95 and 0.94 (2×s, 9H), 0.29, 0.27, 0.26 and 0.25 (4×s, 6H).

The latter mixture was dissolved in benzene (2 mL) together with 2,2'-azobisisobutyronitrile (AIBN, 1 mg). The solution was added to a refluxing solution of $Bu_3SnH$ (0.17 mL, 0.62 mmol) in benzene over a 15 min period using a syringe pump. The resulting solution was heated at reflux for 1 h, then cooled to room temperature and the residue subjected to flash chromatography ($SiO_2$, 40% EtOAc in hexane) to afford 4(R)-(2-thiazoylmethyl)-1-(tert-butyldimethylsilyl)azetidin-2-one (45 mg, 51% yield). $^1$H-NMR (400 MHz, $CDCl_3$) δ7.73 (d, J=3.2 Hz, 1H), 7.25 (d, J=3.2 Hz, 1H), 4.02–3.97 (m, 1H), 3.58 (dd, J=14.8, 3.5 Hz, 1H), 3.19 (dd, J=15.6, 5.4 Hz, 1H), 3.11 (dd, J=14.8, 9.9 Hz, 1H), 2.83 (dd, J=15.6, 2.5 Hz, 1H), 1.00 (s, 9H), 0.31 (s, 3H), 0.28 (s, 3H).

By following the same procedure as in example 1 step E for the deprotection followed by the ureido formation as in example 7, the title compound, 4(R)-thiazolylmethyl)-2-oxoazetidine-1-carboxylic acid N-methyl-N-{{(4-trifluoromethyl)phenyl}methyl}amide, was obtained as a yellow gum. $^1$H-NMR (400 MHz, $CDCl_3$) δ7.72 (d, J=3.3 Hz, 1H), 7.62 (d, J=8.1 Hz, 2H), 7.40 (d, J=8.1 Hz, 2H), 7.25 (d, J=3.3 Hz, 1H), 4.70–4.55 (m, 3H), 3.59 (dd, J=14.9, 4.2 Hz, 1H), 3.45 (dd, J=14.9, 6.9 Hz, 1H), 3.10–3.00 (m, 2H), 2.97 (s, 3H); IR (neat) ν1780, 1669 cm$^{-1}$; FAB-MS m/z 384.2 (MH$^+$); HRMS calcd for $C_{17}H_{16}F_3N_3O_2S$: 384.0994 (MH$^+$); found: 384.1003.

Example 12

4(R)-(2-methyl-2H-tetrazol-5-ylmethyl)-2-oxoazetidine-1-carboxylic acid N-methyl-N{{(4-trifluoromethyl)phenyl}methyl}amide. $R_1=R_2=R_3=$ H, $R_4$=Me, $R_5=CH_2$-(4-$CF_3$-Ph), Z=2-methyl-2H-tetrazolyl) (table 2, entry 223)

The same procedure as in example 7 was followed, but using 4(R)-(2-methyl-2H-tetrazol-5-ylmethyl)azetidine-2-one (that was obtained using published procedures of J. Fetter; E. Keskeny; T. Czuppon; K. Lempert; M. Kajtar-Peredy; J. Tamas. *J. Chem. Soc. Perkin Trans.* 1992, 1, 3061–3067 and L. T. Giang; J. Fetter; K. Lempert; M. Kajtar-Peredy; A. Gomory; *Tetrahedron,* 1996, 52, 10169–10184). After ureido formation the title compound was obtained as a yellow gum. $^1$H-NMR (400 MHz, $CDCl_3$) δ7.56 (d, J=8.0 Hz, 2H), 7.35 (d, J=8.0 Hz, 2H), 4.70–4.44 (m, 3H), 4.21 (s, 3H), 3.40 (dd, J=15.0, 4.1 Hz, 1H), 3.28 (dd, J=15.0, 6.5 Hz, 1H), 3.03 (dd, J=16.0, 6.0 Hz, 1H) 2.90 (s, 3H), 2.83 (dd, J=16.0, 3.7 Hz, 1H); IR (neat) ν1779, 1669, 1322 cm$^{-1}$; FAB MS m/z 383.1 (MH$^+$); HRMS calcd for $C_{16}H_{18}F_3N_6O_2$: 383.1444; found 383.1452.

Example 13

The following two assays (A and B) were used to evaluate anti HCMV activity.
A. HCMV $N_O$ Protease Assay Material & Methods: Fluorescence measurements were recorded on a Perkin-Elmer LS-50B spectrofluorimeter equipped with a plate reader accessory. UV measurements were recorded on a Thermomax® microplate reader from Molecular Devices Corporation, Menlo Park, Calif., USA.

HCMV $N_O$ protease was assayed with an internally quenched fluorogenic substrate based on the maturation cleavage site (Abz-VVNASSRLY(3-$NO_2$)R—OH, $k_{cat}/K_M$=260 M$^{-1}$s$^{-1}$). The fluorescence increase upon cleavage of the Ala-Ser amide bond was monitored using excitation λ=312 nm (slit 2.5 nm) and emission λ=415 nm (slit 5 nm). A protocol adaptable to a 96-well plate format was designed for the determination of IC$_{50}$ values of inhibitors. Briefly, HCMV $N_O$ was incubated for 2½ h at 30° in presence of the substrate with a range of sequentially diluted inhibitors concentrations (300 to 0.06 μM depending on the potency of each compound). After this period, enzymatic hydrolysis of the fluorogenic substrate in the absence of inhibitor led to about a 30% conversion. Quenching was not required before fluorescence measurement since the total scanning time by the plate reader accessory was brief relative to the duration of the reaction. The aqueous incubation buffer contained 50 mM tris(hydroxymethyl)aminomethane.HCl pH 8, 0.5M $Na_2SO_4$, 50 mM NaCl, 0.1 mM EDTA, 1 mM tris(2-carboxyethyl)phosphine.HCl, 3% v/v DMSO and 0.05% w/v casein. The final concentrations of HCMV $N_O$ protease (expressed in terms of total monomer concentration) and substrate were 100 nM and 5 μM respectively. IC$_{50}$ values were obtained through fitting of the inhibition curve to a competitive inhibition model using SAS NLIN procedure. The mode of inhibition was determined by measurements of the initial rates (in cuvettes) at various substrate concentrations in the buffer as described above. The IC$_{50}$ values listed in the following tables the IC$_{50}$ were obtained according to this assay.
B. Plaque Reduction Assay (PRA)

Hs-68 cells (ATCC #CRL 1635) were seeded in 12-well plates at 83,000 cells/well in 1 mL of DMEM medium (Gibco Canada Inc.) supplemented with 10% fetal bovine serum (FBS, Gibco Canada Inc.). The plates were incubated for 3 days at 37° to allow the cells to reach 80–90% confluency prior to the assay.

The medium was removed from the cells by aspiration. The cells were then infected with approximately 50 PFU of HCMV (strain AD169, ATCC VR-538) in DMEM medium supplemented with 5% inactivated FBS (assay medium). (DMEM medium is commercially available and has been described by R. Dulbecco et al., *Virology* 1959, 8, 396.) The virus was allowed to adsorb to cells for 2 h at 37°. Following viral adsorption, the medium was removed from the wells by aspiration. The cells were then incubated with or without 1 mL of appropriate concentrations of test reagent in assay medium. Occasionally, test compounds were added 24 h post-infection. After 4 days of incubation at 37°, the medium was exchanged with fresh medium containing test compound and 4 days later the cells were fixed with 1% aqueous formaldehyde and stained with a 2% violet solution in 20% ethanol in water. Microscopic plaques were counted using a stereomicroscope. Drug effects were calculated as a percent reduction in the number of plaques in the presence of each drug concentration compared to the number observed in the absence of drug. Ganciclovir was used as a positive control in all experiments.

The EC$_{50}$ values obtained according to this assay for certain azetidine derivatives of this invention are listed in the following table under the heading EC$_{50}$.

Example 14

In conjunction with the appropriate starting materials and intermediates, the procedures of examples 1 to 11 can be used to prepare other compounds of formula 1. Examples of compounds thus prepared are listed in the following Tables I, II and III together with mass spectrum data for the compounds, and results from the assays A and B of example 12. Cytotoxic effects noted as TC$_{50}$ in the following tables were determined according to the tetrazolium salt (MTT) metabolic assay, F. Denizot and F. Lang, *J. Immun. Meth.,* 1986, 89, 271.

Symbols used in the following tables include 4-AcNH-Ph: 4-(acetylamino)phenyl; 4-$NH_2$-Ph: 4-aminophenyl;

BTZ: benzothiazolyl; Bu: butyl; 4-CF$_3$-Ph: 4-(trifluoromethyl)phenyl; 4-Cl-Ph: 4-chlorophenyl; 4-COOMe-Ph: 4-(methoxycarbonyl)phenyl; Et: ethyl; 4-F-Ph: 4-fluorophenyl; 4-I-Ph: 4-iodophenyl; 4-isoPr-Ph: 4-(1-methylethyl)phenyl; Me: methyl; 4-MeO-3,5-Me$_2$-Ph: 4-methoxy-3,5-dimethylphenyl; 4-MeO-Ph: 4-methoxyphenyl; 4-Me-Ph: 4-methylphenyl; 2-NO$_2$-Ph: 2-nitrophenyl; 4-NO$_2$-Ph: 4-nitrophenyl; Ph: phenyl; Pr: propyl; 4-Py: 4-pyridinyl; 1-(4-Py)-Pr: 1-(4-pyridinyl) propyl); 4-SCF$_3$-Ph: 4-{(trifluoromethyl)thio}phenyl; 4-SOCF$_3$-Ph: 4-{(trifluoromethyl) sulfinyl}phenyl; 4-SO$_2$CF$_3$-Ph: 4-{(trifluoromethyl)sulfonyl}phenyl; THZ: thiazolyl.

TABLE I

Compound of formula 1 having the structure

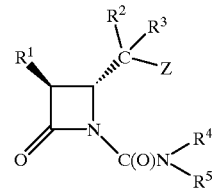

wherein R$^1$, R$^2$ and R$^3$ each is hydrogen, Z is phenyl and R$^4$ and R$^5$ are designated as follows:

| Entry No. | R$^4$ | R$^5$ | IC$_{50}$ μM | EC$_{50}$ μM | TC$_{50}$ μM | FAB/MS (MH$^+$) |
|---|---|---|---|---|---|---|
| 101 | H | 4-F—Ph | 3.7 | >250 | >250 | 299 |
| 102 | H | 4-MeO—Ph | 3.9 | 215 | >250 | 311 |
| 103 | H | 4-Me—Ph | 5.3 | >250 | >250 | 295 |
| 104 | H | Ph | 3.1 | >250 | >250 | 281 |
| 105 | H | 1(R)-(1-naphthalenyl)ethyl | 7.7 | >18 | >18 | 359 |
| 106 | H | 4-MeO-3,5-Me$_2$—Ph | 2.4 | 190 | >250 | 339 |
| 107 | H | 4-Py | 1.9 | >250 | >250 | 282 |
| 108 | H | 1(S or R)—(4-Py)—Pr | 28 | | | 324 |
| 109 | H | 1(R or S)—(4-Py)—Pr | 1.6 | 130 | >250 | 324 |
| 110 | H | Et$_2$CH | 38 | | | 275 |
| 111 | H | (5-benzo[1,3]dioxolyl)methyl | 3.7 | >150 | >150 | 330 |
| 112 | Me | CH$_2$Ph | 10 | 150 | >150 | 309 |
| 113 | Me | CH$_3$ | 50 | | | 233.1 |
| 114 | Me | CH$_2$CH$_2$Ph | 38 | | | 323.2 |
| 115 | Me | CH$_2$COOCH$_2$Ph | 11.7 | | | 367 |
| 116 | H | CH$_2$—Ph | 8.9 | 53 | >250 | 295.2 |
| 117 | Et | CH$_2$—Ph | 42 | | | 323.2 |
| 118 | H | 1(R)-Ph—Pr | 2.6 | 180 | >250 | 323.2 |
| 119 | Me | 1(R)-Ph—Et | 24 | | | 323 |
| 120 | Me | 1(S)-Ph—Et | 17.7 | | | 323 |
| 121 | H | 1(R)-Ph—Bu | 3.4 | 160 | >250 | 337 |
| 122 | Me | CH$_2$-(4-NO$_2$—Ph) | 1.5 | 105 | >250 | 354.2 |
| 123 | Me | 1(R)—Ph—Pr | 30 | | | 337.3 |
| 124 | Me | CH$_2$-(2-NO$_2$—Ph) | 6.9 | 150 | >250 | 354.2 |
| 125 | Me | CH$_2$-(4-NH$_2$—Ph) | 13.4 | | | 324.3 |
| 126 | Me | CH$_2$-(4-Cl—Ph) | 6.9 | 150 | >250 | 343.2 |
| 127 | H | 1(S or R)-(4-Py)—Pr | 28 | | | 338 |
| 128 | H | 1(R or S)-(4-Py)—Pr | 1.6 | 110 | >250 | 338 |
| 129 | Me | CH$_2$-(4-Me—Ph) | 8.9 | 140 | >200 | 323.2 |
| 130 | Me | CH$_2$-(4-MeO—Ph) | 7.4 | 110 | >250 | 339.2 |
| 131 | Me | CH$_2$-(4-COOMe—Ph) | 2.5 | 140 | >250 | 367.2 |
| 132 | Me | CH$_2$-(4-AcNH—Ph) | 17 | 150 | >250 | 366 |
| 133 | Me | CH$_2$-(3-NO$_2$—Ph) | 6.9 | 170 | >250 | 354 |
| 134 | Me | CH$_2$-(4-isoPr—Ph) | 6.4 | 150 | 200 | 351 |
| 135 | Me | CH$_2$-(4-CF$_3$—Ph) | 3.7 | 190 | >250 | 377 |
| 136 | H | CH$_2$-(4-Py) | 13 | >250 | >250 | 296.1 |
| 137 | Me | CH$_2$-(4-SCF$_3$—Ph) | 6.9 | >250 | >250 | 409 |
| 138 | Me | CH$_2$-(4-SOCF$_3$—Ph) | 8.7 | >250 | >250 | 425 |
| 139 | Me | CH$_2$-(4-SO$_2$CF$_3$—Ph) | 4.3 | >250 | >250 | 441 |
| 140 | H | 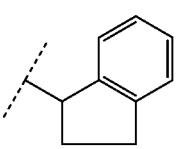 | 14 | | | 321.2 |

TABLE I-continued

Compound of formula 1 having the structure

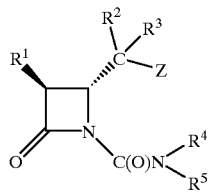

wherein $R^1$, $R^2$ and $R^3$ each is hydrogen, Z is phenyl and $R^4$ and $R^5$ are designated as follows:

| Entry No. | $R^4$ | $R^5$ | $IC_{50}$ $\mu M$ | $EC_{50}$ $\mu M$ | $TC_{50}$ $\mu M$ | FAB/MS $(MH^+)$ |
|---|---|---|---|---|---|---|
| 141 | H | (S)-1-phenylethyl | 42 | | | 309 |
| 142 | H | CH$_2$-(3-Py) | 9.7 | >250 | >250 | 296 |
| 143 | H | CH$_2$-(2-Py) | 33 | | | 296 |
| 144 | H | CH$_2$—CH$_2$—Ph | 29 | | | 309.2 |
| 145 | Me | CH$_2$-(4-CN-Ph) | 6.1 | 120 | >250 | 334 |
| 146 | Me | CH$_2$-(4-NHC(O)CH=CH$_2$-Ph) | 30 | | | 268.1 |

TABLE II

Compounds of formula 1 having the structure

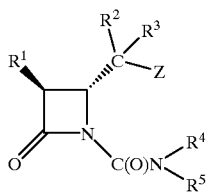

wherein $R^1$, $R^2$, $R^3$, $R^4$, $R^5$ and Z are designated as follows:

| Entry No. | $R^1$ | $R^2$ | $R^3$ | $R^4$ | $R^5$ | Z | $IC_{50}$ $\mu M$ | $EC_{50}$ $\mu M$ | $TC_{50}$ $\mu M$ | FAB/MS $(MH^+)$ |
|---|---|---|---|---|---|---|---|---|---|---|
| 201 | Me | H | H | H | CH$_2$-(4-Py) | Ph | 12 | 190 | >250 | 310 |

TABLE II-continued

Compounds of formula 1 having the structure

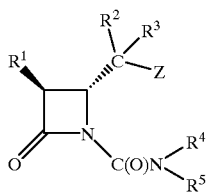

wherein $R^1$, $R^2$, $R^3$, $R^4$, $R^5$ and Z are designated as follows:

| Entry No. | $R^1$ | $R^2$ | $R^3$ | $R^4$ | $R^5$ | Z | $IC_{50}$ μM | $EC_{50}$ μM | $TC_{50}$ μM | FAB/MS (MH$^+$) |
|---|---|---|---|---|---|---|---|---|---|---|
| 202 | Et | H | H | H | CH$_2$-(4-Py) | Ph | 58 | | | 324.2 |
| 203 | Me | H | H | H | Ph | Ph | 0.81 | >250 | >250 | 295.2 |
| 204 | Me | H | H | H | 4-Py | Ph | 0.97 | 205 | >250 | 296.3 |
| 205 | Me | H | H | H | 1(S or R)-(4-Py)—Pr | Ph | 21 | >250 | >250 | 338 |
| 206 | Me | H | H | H | 1(R or S)-(4-Py)—Pr | Ph | 3.2 | 96 | >250 | 338 |
| 207 | Me | H | H | H | CH$_2$Ph | Ph | 5.3 | 140 | >250 | 309.3 |
| 208 | Me | H | H | Me | CH$_2$Ph | Ph | 4.2 | 150 | >250 | 323.3 |
| 209 | MeS | H | H | H | 1(R)—Ph—Pr | Ph | 4.7 | 27 | >250 | 369 |
| 210 | MeO | H | H | H | CH$_2$-(4-Py) | Ph | 2.1 | 210 | >250 | 326 |
| 211 | H | H | H | H | CH$_2$-(4-Py) | (4-I—Ph) | 8.6 | >100 | >100 | 422.1 |
| 212 | H | H | H | H | 1(R)—Ph—Pr | CH$_2$Ph | 4.3 | 140 | >250 | 337.3 |
| 213 | H | H | Me | H | 1(R)—Ph—Pr | Me | 5.9 | 210 | >250 | 275 |
| 214 | H | H | H | H | 1(R)—Ph—Pr | Me | 7.6 | 180 | >250 | 261.1 |
| 215 | H | Me | Me | H | 1(R)—Ph—Pr | Me | 41 | | | 289.1 |
| 216 | H | H | Me | H | 1(R)—Ph—Pr | (R)—Et | 4.4 | 110 | >250 | 289.1 |
| 217 | H | H | Me | H | 1(R)—Ph—Pr | (S)—Et | 11 | 85 | >250 | 289.1 |
| 218 | H | H | H | Me | CH$_2$-(4-CF$_3$—Ph) | (2-THZ) | 5.5 | 78 | 178 | 384.2 |
| 219 | H | H | H | Me | CH$_2$-(4-CF$_3$—Ph) | (2-BTZ) | 0.88 | 110 | >250 | 434 |
| 220 | H | H | H | Me | [CH$_2$-(4-CF$_3$—Ph)] | [phenyloxazole] | 14 | | | 444 |
| 221 | H | H | H | Me | [CH$_2$-(4-CF$_3$—Ph)] | [2-furyl-CH$_2$] | 7.1 | 59 | >100 | 367 |
| 222 | H | H | H | H | [1-Ph-propyl] | [2-Me-tetrazolyl-CH$_2$] | 5 | 125 | >148 | 329 |
| 223 | H | H | H | Me | [CH$_2$-(4-CF$_3$—Ph)] | [2-Me-tetrazolyl-CH$_2$] | 5.7 | 94 | >195 | 383.1 |

TABLE II-continued

Compounds of formula 1 having the structure

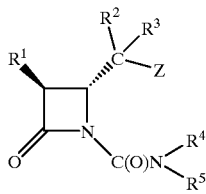

wherein $R^1$, $R^2$, $R^3$, $R^4$, $R^5$ and Z are designated as follows:

| Entry No. | $R^1$ | $R^2$ | $R^3$ | $R^4$ | $R^5$ | Z | $IC_{50}$ μM | $EC_{50}$ μM | $TC_{50}$ μM | FAB/MS ($MH^+$) |
|---|---|---|---|---|---|---|---|---|---|---|
| 224 | H | H | H | Me | 4-NO₂-benzyl | 1-methyl-tetrazol-5-yl-methyl | 2.7 | 100 | >133 | 360 |
| 225 | H | H | H | Me | 4-NO₂-benzyl | benzothiazol-2-yl-methyl | 0.7 | 30 | >50 | 411 |
| 226 | H | H | H | Me | 4-NO₂-benzyl | thien-2-yl-methyl | 1.3 | 70 | >79 | 360 |
| 227 | H | H | H | Me | 4-NO₂-benzyl | thiazol-2-yl-methyl | 2.5 | >29 | >29 | 361 |
| 228 | H | H | H | Me | 4-CF₃-benzyl | thien-2-yl-methyl | 4.5 | >16 | >16 | 383 |
| 229 | H | H | H | Me | 4-NO₂-benzyl | furan-2-yl-methyl | 3.1 | 143 | >261 | 344.1 |
| 230 | H | H | H | Me | 4-CF₃-benzyl | benzimidazol-2-yl-methyl | 2.7 | 11 | >25 | 434 |
| 231 | H | H | H | Me | 4-CF₃-benzyl | 1,3,4-thiadiazol-2-yl-methyl | 2.7 | 11 | >25 | 384 |

TABLE III

Compounds of formula 1 having the structure

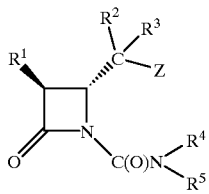

wherein R¹, R² and R³ each is hydrogen, Z is phenyl, and R⁴ and R⁵ together with the nitrogen to which they are attached are designated as follows:

| Entry No. | R⁴\N\R⁵ | IC$_{50}$ μM | EC$_{50}$ μM | TC$_{50}$ μM | FAB/MS (MH⁺) |
|---|---|---|---|---|---|
| 301 | morpholino | 142 | | | 275.1 |
| 302 | 2-(3,4-dihydro-1H-isoquinolinyl) | 36 | | | 321 |
| 303 | pyrrolidino | 63 | | | 259 |
| 304 | 1-(3,4-dihydro-1H-isoquinolinyl) | 154 | | | 321.2 |

What is claimed is:
1. A compound of formula (1)

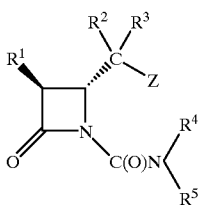
(1)

wherein R¹ is hydrogen, methyl, ethyl, methoxy or methylthio;
R² and R³ each independently is hydrogen or lower alkyl;
R⁴ is hydrogen or lower alkyl;
R⁵ is lower alkyl, lower cycloalkyl, CH$_2$C(O)OR⁶
  wherein R⁶ is methyl, ethyl or phenylmethyl; phenyl, phenyl monosubstituted, disubstituted or trisubstituted with a substituent selected independently from the group consisting of lower alkyl, lower alkoxy, lower alkylthio, halo, hydroxy and amino; phenyl (lower alkyl), phenyl(lower alkyl) monosubstituted or disubstituted on the phenyl portion thereof with a substituent selected independently from the group consisting of lower alkyl, lower alkoxy, lower alkylthio, halo, hydroxy, nitro, amino, lower alkyl amino, di(lower alkyl)amino, lower alkyl-C(O)NH—, di(lower alkyl)aminocarbonyl, cyano, trifluoromethyl, (trifluoromethyl)thio, (trifluoromethyl)sulfinyl, (trifluoromethyl)sulfonyl and C(O)OR⁷ wherein R⁷ is methyl, ethyl or phenylmethyl;
Het or Het(lower alkyl) wherein Het is 2-furyl, 2-methyl-3-furyl, 2-thienyl, 2-pyridinyl, 3-pyridinyl, 4-pyridinyl, 3-methyl-2-pyrrolyl, 2-thiazolyl, 4-thiazolyl, 2-isoxazolyl, 2-pyrimidinyl, 4-methyl-2-pyrimidinyl, 4,6-dimethyl-2-pyrimidinyl, 4-pyrimidinyl, 2,6-dimethyl-2-pyrimidinyl or 4-methyltetrazolyl;
(5-benzo[1,3]dioxolyl)methyl, 1(R)-(1-naphthalenyl) ethyl, 2-benzothiazolyl or 2-thiazolo[4,5-b] pyridinyl; or
R⁴ and R⁵ together with the nitrogen atom to which they are attached form a pyrrolidino, piperidino, morpholino, N-methylpiperazino, 1-(3,4-dihydro-1H-isoquinolinyl) or 2-(3,4-dihydro-1H-isoquinolinyl);
and Z is lower alkyl, phenyl, phenyl monosubstituted or disubstituted with a substituent selected independently from lower alkyl, lower alkoxy, halo, hydroxy and amino; phenylmethyl, phenylmethyl monosubstituted or disubstituted on the phenyl portion thereof with a substituent selected from the group consisting of lower alkyl, lower alkoxy, halo, hydroxy and amino; or (CH$_2$)$_p$-(Het) wherein p is the integer 0 or 1 and Het is a monovalent five or six membered saturated or unsaturated heterocycle containing from one to four heteroatoms selected from N, O or S, said Het being optionally mono- or di-substituted with N-oxido, lower alkyl, phenyl-(C$_{1-3}$) alkyl, lower alkoxy, halo or amino, and said Het being optionally fused to a phenyl ring; with the proviso that when Z is (CH$_2$)$_p$-(Het) as defined herein then R² and R³ each is hydrogen.
2. A compound of formula (1)

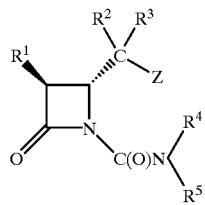
(1)

wherein R¹ is hydrogen, methyl, ethyl, methoxy or methylthio;
R² and R³ each independently is hydrogen or lower alkyl;
R⁴ is hydrogen, lower alkyl, methoxy, ethoxy or benzyloxy;
R⁵ is lower alkyl, lower cycloalkyl, (CH$_2$)$_m$C(O)OR⁶
  wherein m is the integer 1 or 2 and R⁶ is lower alkyl or phenyl(lower alkyl); phenyl, phenyl monosubstituted, disubstituted or trisubstituted with a substituent selected independently from the group consisting of:
    lower alkyl, lower alkoxy, lower alkylthio, halo, hydroxy and amino; phenyl(lower alkyl), phenyl (lower alkyl) monosubstituted or disubstituted on the phenyl portion thereof with a substituent selected independently from the group consisting of lower alkyl, lower alkoxy, lower alkylthio, halo, hydroxy, nitro, amino, lower alkylamino, di(lower alkyl)amino, lower alkyl-C(O)NH—, di(lower alkyl)aminocarbonyl, cyano, trifluoromethyl, (trifluoromethyl)thio, (trifluoromethyl)sulfinyl, (trifluoromethyl)sulfonyl and C(O)OR⁷ wherein R⁷ is lower alkyl or phenyl(lower alkyl);
  Het or Het(lower alkyl) wherein Het represents a monovalent five or six membered saturated or unsaturated heterocycle containing one to two heteroatoms selected from N, O or S, said Het being optionally mono- or di-substituted with lower alkyl, lower alkoxy, halo and/or hydroxy;
  5-(benzo[1,3]dioxolyl)methyl, (1(R)-1-naphthalenyl) ethyl, 2-benzothiazolyl or 2-thiazolo[4,5-b] pyridinyl; or R⁴ and R⁵ together with the nitrogen atom to which they are attached form a piperidino, morpholino, thiomorpholino, piperazino, N-methylpiperazino, 1-(3, 4-dihydro-1H-isoquinolinyl) or 2-(3,4-dihydro-1H-isoquinolinyl) or a pyrrolidino ring optionally substituted with C(O)Obenzyl or with phenyl said phenyl ring optionally mono- or di-substituted with a substituent selected independently from the group consisting of lower alkyl, lower alkoxy, lower alkylthio, halo, hydroxy, nitro, amino, lower alkylamino, di(lower alkyl)amino, lower alkyl-C(O)NH—, di(lower alkyl) aminocarbonyl, cyano, trifluoromethyl, (trifluoromethyl)thio, (trifluoromethyl)sulfinyl, (trifluoromethyl)sulfonyl and C(O)OR₇ wherein R₇ is lower alkyl or (lower alkyl)phenyl; and Z is lower alkyl, phenyl, phenyl monosubstituted or disubsituted with a substituent selected independently from lower alkyl, lower alkoxy, halo, hydroxy and amino; phenylmethyl, phenylmethyl monosubstituted or disubstituted on the phenyl portion thereof with a substituent selected from the group consisting of lower alkyl, lower alkoxy, halo, hydroxy and amino; or (CH₂)$_p$-(Het) wherein p is the integer 0 or 1 and Het is a monovalent five or six membered saturated or unsaturated heterocycle containing from one to four heteroatoms selected from N, O or S, said Het being optionally mono- or di-substituted with N-oxido, lower alkyl, phenyl-(C$_{1-3}$) alkyl, lower alkoxy, halo or amino, and said Het being optionally fused to a phenyl ring; with the proviso that when Z is (CH₂)$_p$-(Het) as defined herein then R² and R³ each is hydrogen;

or a therapeutically acceptable acid addition salt thereof.

3. The compound according to claim 1 wherein R¹ is hydrogen, methyl, ethyl, methoxy or methylthio;

R² and R³ each independently is hydrogen, or methyl;

R⁴ is hydrogen, methyl, or ethyl;

R⁵ is methyl, ethyl, 1-methylethyl, cyclobutyl, cyclopentyl, cyclohexyl, CH₂C(O)OR⁶ wherein R⁶ is methyl or phenylmethyl;

phenyl, 4-fluorophenyl, 4-methoxyphenyl, 3,5-dimethyl-4-methoxyphenyl, 4-methylphenyl, 4-(methylthio)phenyl, phenylmethyl, phenylethyl, 1-phenylpropyl, 1-phenylbutyl, phenylmethyl monosubstituted at position 3 or 4 of the phenyl portion thereof with a substituent selected from the group consisting of methyl, ethyl, 1-methylethyl, 1,1-dimethylethyl, propyl, methoxy, ethoxy, methylthio, bromo, chloro, fluoro, nitro, acetamido, C(O)NMe₂, C(O)NEt₂, cyano, trifluoromethyl, (trifluoromethyl) thio, (trifluoromethyl)sulfinyl, (trifluoromethyl) sulfonyl and C(O)OR⁷ wherein R⁷ is methyl, ethyl or benzyl;

(5-benzo[1,3]dioxolyl)methyl, 1(R)-(1-naphthylenyl) ethyl, 2-pyridinyl, 4-pyridinyl, 2-pyridinylmethyl, 4-pyridinylmethyl, 1-(4-pyridinyl)ethyl or 1-(4-pyridinyl)propyl; or R⁴ and R⁵ together with the nitrogen to which they are attached form a pyrrolidino, piperidino, morpholino, 1-(3,4-dihydro-1H-isoquinolinyl) or 2-(3,4-dihydro-1H-isoquinolinyl); and Z is phenyl or phenylmethyl.

4. The compound according to claim 2 wherein R¹ is hydrogen, methyl or methylthio;

R² and R³ each independently is hydrogen or methyl;

R⁴ is hydrogen, methyl or ethyl;

R⁵ is methyl, ethyl, 1-methylethyl, cyclobutyl, cyclopentyl, cyclohexyl, CH₂C(O)OR⁶ wherein R⁶ is methyl or phenylmethyl;

phenyl, 4-fluorophenyl, 4-methoxyphenyl, 3,5-dimethyl-4-methoxyphenyl, 4-methylphenyl, 4-(methylthio)phenyl, phenylmethyl, 1-phenylpropyl, 1-phenylbutyl, phenylmethyl monosubstituted at position 3 or 4 of the phenyl portion thereof with a substituent selected from the group consisting of methyl, ethyl, 1-methylethyl, 1,1-dimethylethyl, propyl, methoxy, ethoxy, methylthio, bromo, chloro, fluoro, nitro, acetamido, C(O)NMe₂, C(O)NEt₂, cyano, trifluoromethyl, (trifluoromethyl) thio, (trifluoromethyl)sulfinyl, (trifluoromethyl)-sulfonyl and C(O)OR⁷ wherein R⁷ is methyl, ethyl or benzyl;

(5-benzo[1,3]dioxolyl)methyl, 1(R)-(1-naphthalenyl) ethyl, 2-pyridinyl, 4-pyridinyl, 2 -pyridinylmethyl, 4-pyridinylmethyl, 1-(4-pyridinyl)ethyl or 1-(4-pyridinyl)propyl; and Z is lower alkyl.

5. The compound according to claim 2 wherein R¹ is hydrogen, methyl, methylthio or methoxy;

R² and R³ each independently is hydrogen or methyl;

R⁴ is hydrogen, methyl or ethyl;

R⁵ is methyl, ethyl, 1-methylethyl, cyclobutyl, cyclopentyl, cyclohexyl, CH₂C(O)OR⁶ wherein R⁶ is methyl or phenylmethyl;

phenyl, 4-fluorophenyl, 4-methoxyphenyl, 3,5-dimethyl-4-methoxyphenyl, 4-methylphenyl, 4-(methylthio)phenyl, phenylmethyl, 1-phenylpropyl, 1-phenylbutyl, phenylmethyl monosubstituted at position 3 or 4 of the phenyl portion thereof with a substituent selected from the group consisting of methyl, ethyl, 1-methylethyl, 1,1-dimethylethyl, propyl, methoxy, ethoxy, methylthio, bromo, chloro, fluoro, nitro, acetamido, C(O)NMe₂, C(O)NEt₂, cyano, trifluoromethyl, (trifluoromethyl) thio, (trifluoromethyl)sulfinyl, (trifluoromethyl) sulfonyl and C(O)OR⁷ wherein R⁷ is methyl, ethyl or benzyl;

(5-benzo[1,3]dioxolyl)methyl, 1(R)-(1-naphthalenyl) ethyl, 2-pyridinyl, 4-pyridinyl, 2-pyridinylmethyl, 4-pyridinylmethyl, 1-(4-pyridinyl)ethyl or 1-(4-pyridinyl)propyl; and Z is 2-furyl, 2-thienyl, 2-pyridinyl, 3-pyridinyl, 4-pyridinyl, 3-methyl-2-pyrrolyl, 2-thiazolyl, 2-isoxazolyl, 2-pyrimidinyl, 4,6-dimethyl-2-pyrimidinyl, 5-(1-methyl-1H-tetrazolyl), 5-(2-methyl-2H-tetrazolyl), 2-benzothiazolyl or 2-thiazolo[4,5-b] pyridinyl.

6. The compound according to claim 2 wherein R¹ is hydrogen, methyl, methoxy or methylthio;

R² and R³ each is hydrogen;

R⁴ is hydrogen or methyl;

R⁵ is CH₂C(O)OR⁶ wherein R⁶ is phenylmethyl; or

R⁵ is 4-fluorophenyl, 4-methoxyphenyl, 3,5-dimethyl-4-methoxyphenyl, (4-methylthio)phenyl, phenylmethyl, 1(R)-phenylethyl, 1(S)-phenylethyl, 1(R)-phenylpropyl, 1(R)-phenylbutyl, (4-methylphenyl) methyl, {4-(1-methylethyl)phenyl}methyl, (4-methoxyphenyl)methyl, (4-chlorophenyl)methyl, (2-nitrophenyl)methyl, (3-nitrophenyl)methyl, {4-(acetamido)phenyl}methyl, {4-(trifluoromethyl) phenyl}methyl, {4-{(trifluoromethyl) thio}phenyl}methyl, {4-{(trifluoromethyl) sulfinyl}phenyl}methyl, {4-{(trifluoromethyl) sulfonyl}phenyl}methyl, {4-(methoxycarbonyl)

phenyl}methyl, (5-benzo[1,3]dioxolyl)methyl, 1(R)-(1-naphthalenyl)ethyl, 4-pyridinyl, 4-pyridinylmethyl or 1-(4-pyridinyl)propyl; or $R^4$ and $R^5$ together with the nitrogen to which they are attached form a pyrrolidino, morpholino, 1-(3,4-dihydro-1H-isoquinolinyl) or 2-(3,4-dihydro-1H-isoquinolinyl); and Z is phenyl or phenylmethyl.

7. A pharmaceutical composition for treating cytomegalovirus infections in a mammal, including human, comprising a compound of formula 1 according to claim 2, or a therapeutically acceptable salt thereof, and a pharmaceutically acceptable carrier.

8. A method for treating cytomegalovirus infection in a mammal, including human, comprising administering thereto an effective amount of a compound of formula 1 according to claim 2, or a therapeutically acceptable salt thereof.

9. A method for protecting human cells against cytomegalovirus pathogenesis comprising treating said cells with an anti-cytomegalovirus effective amount of a compound of formula 1 according to claim 2, or a therapeutically acceptable salt thereof.

10. The compound of formula 1 according to claim 2 in combination with anti-herpes compound selected from the group consisting of ganciclovir, forscarnet, acyclovir, valacyclovir, famciclovir, cidofovir, penciclovir, and lobucavir.

11. The compound of formula 1 according to claim 2 in comibnation with anti-retroviral compound selected from the group consisting of reverse transcriptase inhibitors and protease inhibitors.

* * * * *